(12) United States Patent
Hayden

(10) Patent No.: US 10,329,180 B2
(45) Date of Patent: Jun. 25, 2019

(54) AIR CLEANING FOUNTAIN

(71) Applicant: John B. Hayden, Paradise Valley, AZ (US)

(72) Inventor: John B. Hayden, Paradise Valley, AZ (US)

( * ) Notice: Subject to any disclaimer, the term of this patent is extended or adjusted under 35 U.S.C. 154(b) by 99 days.

(21) Appl. No.: 15/495,133

(22) Filed: Apr. 24, 2017

(65) Prior Publication Data

US 2017/0225984 A1    Aug. 10, 2017

Related U.S. Application Data

(63) Continuation-in-part of application No. 15/143,164, filed on Apr. 29, 2016, now Pat. No. 10,143,956,
(Continued)

(51) Int. Cl.
*B01D 53/78* (2006.01)
*C02F 1/72* (2006.01)
(Continued)

(52) U.S. Cl.
CPC ............. *C02F 1/725* (2013.01); *A61L 9/00* (2013.01); *B01D 47/022* (2013.01); *B01D 53/78* (2013.01); *B05B 17/085* (2013.01); *C02F 1/325* (2013.01); *C02F 1/505* (2013.01); *C02F 1/66* (2013.01); *C02F 1/722* (2013.01); *C02F 1/76* (2013.01); *C02F 2103/023* (2013.01); *C02F 2201/009* (2013.01); *C02F 2201/3221* (2013.01); *C02F 2201/3222* (2013.01); *C02F 2303/04* (2013.01);
(Continued)

(58) Field of Classification Search
CPC ........ B01D 53/74; B01D 53/77; B01D 53/78; B01F 3/04

USPC .......................................... 96/322, 326, 277
See application file for complete search history.

(56) References Cited

U.S. PATENT DOCUMENTS

| 386,777 A | 7/1888 | Griesser |
| 999,114 A | 7/1911 | Lang |

(Continued)

FOREIGN PATENT DOCUMENTS

| DE | 37 16 885 A1 | 12/1988 |
| JP | 61-257522 | 11/1986 |

(Continued)

OTHER PUBLICATIONS

"Rainshadow Waterfalls", http://www.rainshadowwaterwalls.com/ date Oct. 9, 2006, pp. 1-2.
(Continued)

*Primary Examiner* — Robert A Hopkins
(74) *Attorney, Agent, or Firm* — Baker & Hostetler LLP

(57) ABSTRACT

A self-cleaning fountain includes: a structure having two ends, defining a first flow way for a first fluid to flow along, wherein the structure defines holes for allowing a second fluid to flow through the holes; a pump system configured to pump the first fluid to a first end of the structure; a distributer located at the first end of the structure and configured to spray the first fluid received from the pump system onto the structure; a catch basin located at a second end of the structure for collecting the first fluid that has moved along the flow way to the catch basin; a photocatalytic coating on the structure; and a light source configured to direct light on the photocatalytic coating.

19 Claims, 19 Drawing Sheets

Related U.S. Application Data which is a continuation-in-part of application No. 14/834,085, filed on Aug. 24, 2015, now Pat. No. 9,868,129.

(51) Int. Cl.

| | | |
|---|---|---|
| *B05B 17/08* | (2006.01) | |
| *B01D 47/02* | (2006.01) | |
| *C02F 1/66* | (2006.01) | |
| *C02F 1/32* | (2006.01) | |
| *C02F 1/50* | (2006.01) | |
| *A61L 9/00* | (2006.01) | |
| *C02F 1/76* | (2006.01) | |
| *C02F 103/02* | (2006.01) | |

(52) U.S. Cl.
CPC ......... *C02F 2305/10* (2013.01); *Y02A 20/212* (2018.01)

(56) References Cited

U.S. PATENT DOCUMENTS

| | | |
|---|---|---|
| 1,139,053 A | 5/1915 | Murray et al. |
| 1,516,167 A | 11/1924 | Hanson |
| 1,631,240 A | 6/1927 | Amet |
| 1,689,790 A | 10/1928 | Lefevre, Jr. |
| 1,837,225 A | 12/1931 | Lipski |
| 1,900,501 A | 3/1933 | Hunt et al. |
| 2,031,055 A | 2/1936 | McKinney |
| 2,778,916 A | 1/1957 | Holloway |
| 3,174,688 A | 3/1965 | Chatten |
| 3,211,378 A | 10/1965 | Zysk |
| 3,568,927 A | 3/1971 | Scurlock |
| 3,743,256 A | 7/1973 | Oplatka |
| 3,778,042 A | 12/1973 | Schade et al. |
| 3,867,485 A | 2/1975 | Yeagle |
| 4,038,347 A | 7/1977 | Mickley |
| 4,234,526 A | 11/1980 | Mackay et al. |
| 4,329,205 A | 5/1982 | Tsumura et al. |
| 4,333,887 A | 6/1982 | Goettl |
| 4,351,781 A | 9/1982 | Blatter |
| 4,353,846 A | 10/1982 | Mehrens et al. |
| 4,443,513 A | 4/1984 | Meitner et al. |
| 4,615,182 A | 10/1986 | Worthington |
| 4,615,844 A | 10/1986 | Dickison et al. |
| 4,747,538 A | 5/1988 | Dunn et al. |
| 4,747,583 A | 5/1988 | Gordon et al. |
| 4,881,280 A | 11/1989 | Lesikar |
| 5,067,653 A | 11/1991 | Araki et al. |
| 5,145,280 A | 9/1992 | Araki et al. |
| 5,154,671 A | 10/1992 | Smollar et al. |
| 5,167,368 A | 12/1992 | Nash |
| 5,226,935 A | 7/1993 | Wolff et al. |
| 5,288,018 A | 2/1994 | Chikazumi |
| 5,313,744 A | 5/1994 | Shank, Jr. |
| 5,314,623 A | 5/1994 | Heskett |
| 5,445,322 A | 8/1995 | Formhals et al. |
| 5,537,696 A | 7/1996 | Chartier |
| 5,732,419 A | 3/1998 | Feist |
| 5,738,280 A | 4/1998 | Ruthenberg |
| 5,794,318 A | 8/1998 | Parker et al. |
| 6,149,070 A | 11/2000 | Hones |
| 6,152,381 A | 11/2000 | Hones |
| 6,311,898 B1 | 11/2001 | Gruff |
| 6,347,750 B1 | 2/2002 | Delettre |
| 6,382,520 B1 | 5/2002 | Hones |
| 6,527,257 B1 | 3/2003 | Schuld |
| 6,626,368 B2 | 9/2003 | Nakayama et al. |
| 6,731,429 B2 | 5/2004 | Lunde |
| 6,759,018 B1 * | 7/2004 | Arno ............... B01D 19/04 261/21 |
| 7,066,452 B2 | 6/2006 | Rotering et al. |
| 7,296,785 B2 | 11/2007 | Hayden |
| 7,344,124 B2 | 3/2008 | Hayden |
| 7,500,656 B2 | 3/2009 | Hayden |
| 7,513,486 B2 | 4/2009 | Bachert |
| 2001/0018776 A1 | 9/2001 | Koren et al. |
| 2001/0055516 A1 | 12/2001 | King et al. |
| 2002/0073720 A1 | 6/2002 | Bourne et al. |
| 2006/0078458 A1 | 4/2006 | Strobl et al. |
| 2006/0137380 A1 * | 6/2006 | Reinders ............ F24F 5/0035 62/304 |
| 2006/0208369 A1 | 9/2006 | Hayden |
| 2010/0001092 A1 | 1/2010 | Kloppenberg |
| 2013/0146783 A1 | 6/2013 | Boodaghians et al. |
| 2015/0219346 A1 | 8/2015 | Morikawa et al. |
| 2017/0056808 A1 | 3/2017 | Hayden |

FOREIGN PATENT DOCUMENTS

| | | |
|---|---|---|
| JP | 3-167542 | 7/1991 |
| JP | 2002-248391 | 9/2002 |
| KR | 100740668 B1 | 7/2007 |
| KR | 200441741 Y1 | 9/2008 |
| KR | 101417868 B1 | 7/2014 |
| WO | 2008142866 A1 | 11/2008 |

OTHER PUBLICATIONS

"Water Wall", manufacturedd by Kabana Kascade, RainShadow-WaterWalls.com, date Apr. 16, 2007, 8 pages.
International Search Report issued in International Patent Application No. PCT/US16/48158 dated Jan. 26, 2017.
(Exalted Fountains LLC) Copper Screen Falla With Premium Industrial Grade Copper., Jan. 23, 2015; second page, second, fourth paragraphs downloaded Oct. 7, 2016 from: http://www.exaltedfountains.com/floorfountains/aiwcopperscreenfalls.html.
U.S. Office Action dated Mar. 10, 2017, in U.S. Appl. No. 14/834,085.
Wu, et al., "Photocatalysts of Titanium Dioxide for Water Disinfection: Challenges and Future Perspectives", International Journal of Photochemistry, vol. 2014 (2014), Article ID 973484, http://dx.doi.org/10.1155/2014/97348.
"Copper Screen Falls With Premium Industrial Grade Copper"; Exalted Fountains; Jan. 23, 2015; retrieved from the internet http://web.archive.org/web/20150123102851/http://www.exaltedfountains.com:80/floor-fountains/aiw-copper-screen-falls.html; p. 1.
"Copper Screen Falls—Plumbing Spec Sheet"; Jul. 21, 2013; retrieved from the internet http:/web.archive.org/web/20130721183350/http://www.exaltedfountains.com/aiw-filtration.pdf#close; p. 1.

* cited by examiner

AIR CLEANING FOUNTAIN

CROSS-REFERENCE TO RELATED APPLICATIONS

This application claims priority to, and is a continuation-in-part, of U.S. patent application entitled, AIR CLEANING FOUNTAIN, filed Apr. 29, 2016, having Ser. No. 15/143,164, now pending, which is a continuation-in-part of U.S. patent application entitled, AIR CLEANING FOUNTAIN, filed Aug. 24, 2015, having a Ser. No. 14/834,085, now pending, the disclosures of which are hereby incorporated by reference in their entirety.

FIELD OF THE INVENTION

The present invention relates generally to an air cleaning fountain apparatus. More particularly, the present invention relates to a film or sheet-type water curtain apparatus and method that cleans ambient air and cleans the water or fluid used in the fountain.

BACKGROUND OF THE INVENTION

Water from a reservoir running over a dam, in such a manner as to create a dispersion, is noted to produce aesthetically and acoustically pleasing effects, including a cooling effect as well as a change in humidity in areas nearby. It is noted that this same effect can be duplicated in an artificial waterfall by using a thin angled panel, and allowing water to run down the panel. This panel may also have indentures that cause a rippling effect in the falling water.

Cooling our dwellings and workspace today is comprised of two subgroups primarily, heat exchange and evaporative cooling. Heat exchange air conditioning, the most popular, consumes large amounts of electricity, and uses chemicals to transport heat that are considered potentially harmful to the environment.

In addition, heat exchange releases excess heat back into the environment, but recycles the same air over and over again. The "swamp" evaporative cooler is effectively a box containing a fan that draws air through saturated pads to provide cooling and a pump to keep the pads moist. It has remained the same for many decades.

A variation of these subgroups uses evaporation to cool a heat exchanger then passes the cooled air through wet pads, thus reducing humidity. Limitations are inherent to ambient humidity reducing efficacy, and the large volumes of air that must be moved. The use of evaporative cooling and air conditioning when run simultaneously in an area cancel out their cooling benefits, since one introduces humidity and the other removes humidity. Neither of these will work in a passive way since both require energy from an external source.

The recent popularity of misting systems shows that a need for cooling outdoor areas is desirable. These however release large volumes of water into the air and can saturate objects nearby. They are additionally prone to clogging due to mineralization and since they rely on high pressure to mist flooding can occur if compromised.

Furthermore, indoor air purification systems require constant cleaning and electricity to function. These systems only clean air once it is inside by recirculation.

Waterfalls such as those represented by the prior art allow water to collect in an upper reservoir, flow down an angled surface, and collect in a lower reservoir. The water is then re-circulated to the upper reservoir using a pump means, whereby the cycle may repeat.

U.S. Pat. No. 5,167,368 to Nash shows a waterfall providing a natural waterfall effect with accompanying acoustical effects.

U.S. Pat. No. 3,211,378 to Zysk is a wall fountain having a pool of water and a pump for raising water from the pool to a higher lever where it then falls over a vertical wall back into the pool.

The waterfalls described previously, and others like them, all suffer from a number of distinct disadvantages, such as considerable water droplet splashing over a range of several feet from the base of the waterfalls; significant evaporation of water to the point that refill may be required daily; risk of water spillage during relocation of the waterfall; and a large base to house a lower reservoir and a means for returning water to the upper reservoir.

Moreover, conventional decorative water or waterfall displays are typically constructed for indoor or outdoor use. These water or waterfall displays generally use a plurality of water chambers and wide, flat spouts to create thick and discontinuous streams of water that fall a short distance into the pool or spa below. One of the problems with such devices is that they are primarily designed for use with large volumes of water, which makes it difficult to use the devices in indoor water displays. Moreover, such prior art waterfall displays do not form a continuous film or layer of downwardly flowing water, but rather form thick, turbulent streams which tend to splash and are not particularly attractive as a decorative display. Additionally, the waterfall produced by such devices tends to separate into one or more generally cylindrical streams of water as it falls because of the strong surface tension of water that tends to pull the water flow together. Examples of such devices are disclosed in U.S. Pat. No. 4,881,280 to Lesikar; U.S. Pat. No. 5,537,696 to Chartier; and U.S. Pat. No. 5,738,280 to Ruthenberg.

Decorative indoor water displays are known in the art. However, the known indoor water displays do not create an unsupported film or laminar sheet of water. Instead, such displays are characterized by flowing water over a solid or broken solid surface, such as an inclined or vertical plate. The water adheres to the plate surface as it cascades down. Such displays do not create a transparent film of water, but merely flow water over an existing structure to create a rippling effect. An example of such a device is disclosed in U.S. Pat. No. 4,747,538 to Dunn et al.

Indoor displays that are used to advertise oil are known in the art. One of the problems associated with the existing advertising display devices is that in order to function, they require the use of viscous fluids, such as lubricating oil. U.S. Pat. No. 1,689,790 to Lefevre, Jr. discloses an oil display device. Lefevre, Jr. however, is limited to maintaining a thin film of viscous liquid. The device relies on the high viscosity of the liquid displayed to create a film. Another problem associated with the Lefevre, Jr. device is that in order to maintain contact between the viscous liquid and two guides, it relies on forming the guides such that they converge at the bottom of the device. As a result of these deficiencies, the device disclosed would not be able to maintain a film of aqueous liquid. Similarly, U.S. Pat. No. 1,837,225 to Lipski discloses an oil display device for displaying cyclic movement of an oil film, and is adapted for use only with lubricating oils and other liquids with high molecular adhesion. The Lipski device is similarly not suited for low viscosity liquids, such as water or aqueous liquids which have low molecular adhesion and high molecular cohesion.

The creation of water screens is not new and numerous procedures are already in use. However the apparatus and materials conventionally implemented present major drawbacks due to complexity of operation, restrictive dimensions, low mechanical ruggedness, bad endurance over time and vulnerability to bad weather.

Accordingly, until now the proposed systems fail to meet a certain number of requirements. In contrast, the present invention presents a high degree of flexibility in terms of size and shape, and offers a great mobility at low construction and maintenance costs.

The adaptability of the process is based on a combination of several significant innovations, such as air permeability and visual transparency thanks to the size of the net mesh; large span construction scalable in terms of both height and width lightness and tolerance thanks to multiple adjustment points; and low volume reservoirs thanks to a maximum water spread.

Furthermore, it is well known to capture paint overspray whether as a liquid or as a powder by use of water curtains which are placed behind the substrate being painted. The water curtains are provided by directing water downward on a flat support to form a coherent sheet of water which catches the paint particles or droplets. Similarly, the present invention may be configured to passively filter air by placing the water curtain across an opening or passageway allowing filtered air to pass through while increasing its humidity, providing cooling effects and reducing the particulate matter therein.

One potential issue with some water curtains is that the water or fluid that flows over the curtain may subject to biofouling or dirty over time due biomass to other undesired particles in the liquid. The biofouling may be result of bacteria, algae, parasites, viruses, fungi or other undesirable substances in the liquid. The other undesired particles may include, but are not limited to just, dirt, sand or any other particulate or soluble foreign objects finding their way into the fluid. Furthermore, features of the water or fluid curtain may start to corrode over time. As result, it may be desirable to have a bio-static, corrosion resistant and/or self-cleaning or self-purifying fountain.

The devices disclosed in the aforementioned patents suffer from many deficiencies as described above. Accordingly, it is desirable, therefore, to provide a decorative, useful, educational, and preferably mobile indoor or outdoor waterfall/water curtain which utilizes a low viscosity liquid, such as water or other aqueous liquid, to form an attractive display of a continuous liquid film along a material drape in order to provide evaporative cooling and filtration of the ambient air.

SUMMARY OF THE INVENTION

The foregoing needs are met, to a great extent, by the present invention, wherein in one aspect an apparatus is provided that in some embodiments may include a decorative, useful, educational, and preferably mobile indoor or outdoor waterfall/water curtain which utilizes a low viscosity liquid, such as water or other aqueous liquid, to form an attractive display of a continuous liquid film along a material drape in order to provide evaporative cooling and filtration of the ambient air.

In accordance with one aspect of the present invention, fountain is provided. The fountain includes: a drape; a catch basin located below the drape and oriented to catch a fluid flowing at least one of over and through the drape; a conduit fluidly connected to the catch basin forming a circuit to return the fluid in the catch basin to flow at least one of over and through the drape; a pump fluidly connected to the circuit and configured to pump the fluid through the conduit; and at least one of the drape, catch basin, conduit includes surface oriented to contact the fluid and the surface includes at least one of copper and silver.

In yet another embodiment, a fountain is provided. The fountain includes: a drape; a catch basin located below the drape and oriented to catch a fluid flowing at least one of over and through the drape; a conduit fluidly connected to the catch basin forming a circuit to return the fluid in the catch basin to flow at least one of over and through the drape; a pump fluidly connected to the circuit and configured to pump the fluid through the conduit; at least one of the drape, catch basin, conduit includes surface oriented to contact the fluid and the surface wherein at least one of copper and silver; and at least one of either: a) an ultraviolet light configured to shine ultra violet light on fluid in the circuit; and b) an antimicrobial metal located in the circuit and configured to contact fluid in the circuit.

In another embodiment, a fountain is provided. The fountain includes: a drape; a catch basin located below the drape and oriented to catch a fluid flowing at least one of over and through the drape; a conduit fluidly connected to the catch basin forming a circuit to return the fluid in the catch basin to flow at least one of over and through the drape; a pump fluidly connected to the circuit and configured to pump the fluid through the conduit; and an ultra violet light configured to shine on fluid in the circuit.

In another embodiment, a self-cleaning fountain is provided. The self-cleaning fountain includes: a structure having two ends, defining a first flow way for a first fluid to flow along, wherein the structure defines holes for allowing a second fluid to flow through the holes; a pump system configured to pump the first fluid to a first end of the structure; a distributer located at the first end of the structure and configured to spray the first fluid received from the pump system onto the structure; a catch basin located at a second end of the structure for collecting the first fluid that has moved along the flow way to the catch basin; a photocatalytic coating on the structure; and a light source configured to direct light on the photocatalytic coating.

In another embodiment, a method of cleaning a fluid in a fountain includes: providing a first flow path for a first fluid to flow along, wherein the first flow path includes a structure defining holes; orienting the holes to allow a second fluid to flow through the holes and interact with the first fluid; providing a photocatalytic substance along the flow path to contact the first fluid; and orienting lights configured to activate the photocatalytic substance to provide a processing function on the first fluid.

In another embodiment, a self-cleaning fountain is provided. The self-cleaning fountain includes: a structure having two ends, defining a first flow way for a first fluid to flow along, wherein the structure defines holes for allowing a second fluid to flow through the holes; means for moving fluid configured to move the first fluid to a first end of the structure; a distributer located at the first end of the structure and configured to spray the first fluid received from the means for moving fluid onto the structure; means for collecting a fluid located at a second end of the structure for collecting the first fluid that has moved along the flow way to the means for collecting fluid; a photocatalytic coating on the structure; and means for selectively activating the photocatalytic coating to cause the photocatalytic coating to treat the first fluid.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
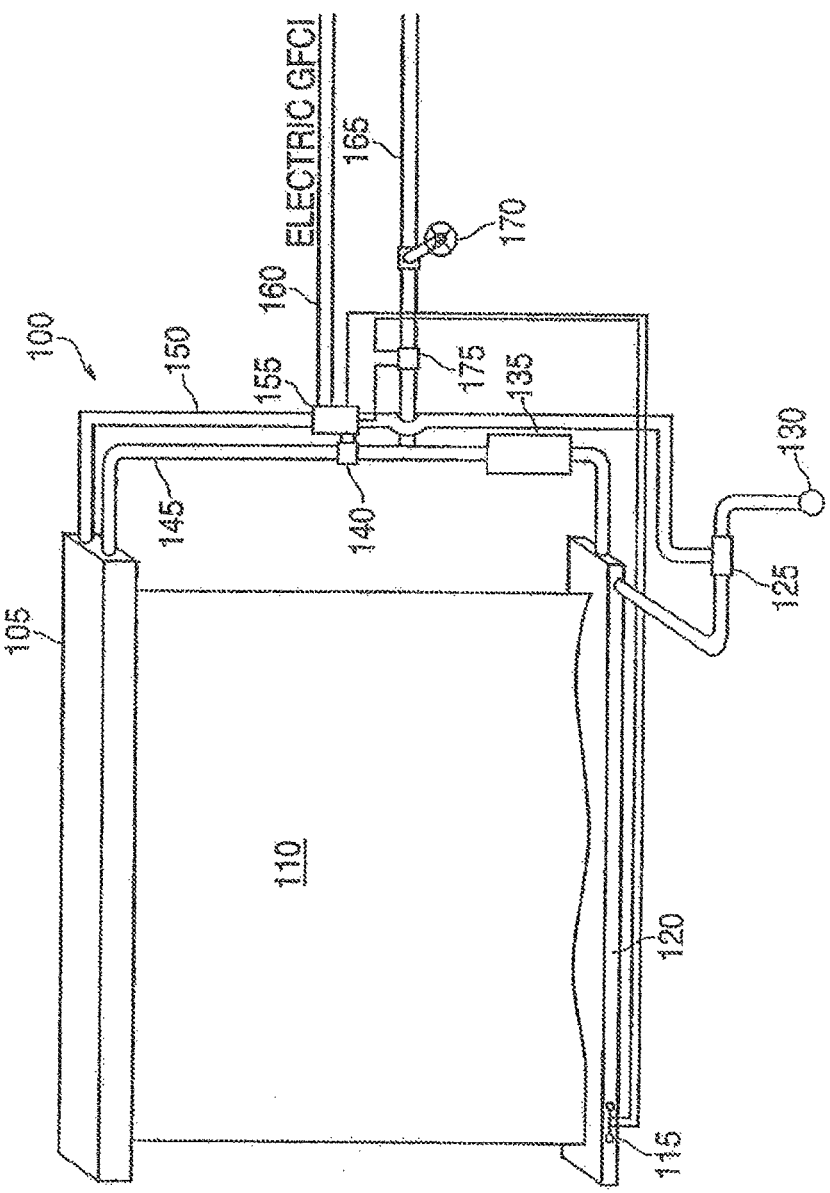
FIG. 1 is a diagrammatic representation of a water curtain apparatus according to a preferred embodiment of the invention.

The invention will now be described with reference to the drawing figures, in which like reference numerals refer to like parts throughout. As shown in FIG. 1, an embodiment in accordance with the present invention provides a water curtain or drape assembly 100 having a drape hood 105, material drape 110, float overflow shut-off 115, collection return 120, a drainage line solenoid 125 which preferably is electric, a drainage line 130, a filter 135, drape solenoid 140 which preferably is electric, a drape feed line 145, a pump 240, a pump power line 150, an on/off switch 155 to a power source 160 which preferably is a ground fault circuit interrupter (GFCI) power line for obvious safety concerns, a feed line 165, and a shutoff valve 170.

The present invention, wherein in one aspect provides that in some embodiments may include a decorative, useful and educational indoor waterfall which utilizes a low viscosity liquid, such as water or other aqueous liquid, to form an attractive display of a continuous liquid film along a material drape 110 between two limiting elements 105, 120. The material drape 110 may be porous or semi-porous and preferably made of a fiber glass mesh fabric.

Figure 2:
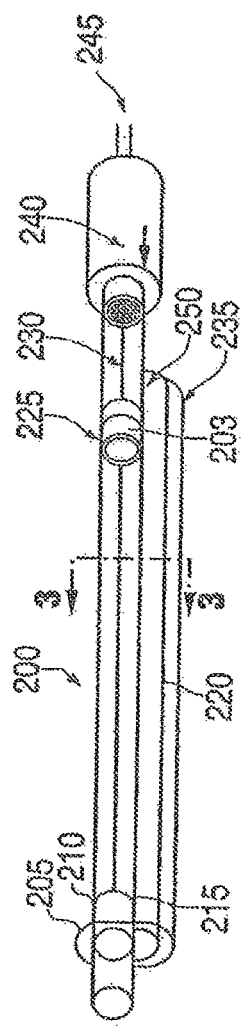
FIG. 2A is a diagrammatic representation of a piston assembly according to a preferred embodiment of the invention.
FIG. 2B is a cross-sectional view taken along the 3-3 in FIG. 2A.

An embodiment of the present inventive apparatus and method is illustrated in FIGS. 1, 2A and 2B, wherein the material drape 100 is disposed within the hood 105 and suspended from the hood 105 towards the collection return 120. As water or other aqueous liquid is fed from feed line 165 to the drape feed line 145 into the hood 105, pump 240 via intake 245 pumps the water or other aqueous liquid into piston assembly 200 having a piston 203, a magnetic collar 205, a piston open position at 210, a gutter 255, a gutter drain slit 215, a gutter groove 220, a piston closed position at 225, an elastic cord 230 attached to piston 203, a drape material track 235, gutter drain 250, and a piston sleeve 260.

The pumped liquid then pressurizes piston sleeve 260 thereby causing piston 203 to move longitudinally along sleeve 260 from the closed position 225 to the open position 210. The magnetic collar 205 may in effect assist in pulling the piston 203 to the open position by using a reverse polarity magnetic collar 205 to attract the piston 203. The elastic cord 230 assists in returning the piston to the closed position 225 upon the reduction or removal of liquid pressure within the piston sleeve 260 accordingly. Drain 250 allows liquid located between the pump 240 and piston 203 at the closed position 225 to be exhausted. Drain slit 215 allows liquid to flow from the piston sleeve 260 into the gutter 255 via the gutter groove 220 and into the material track 235. Once the liquid begins to fill the material track 235, liquid will accumulate and flow upon the material drape 110 disposed within the track 235 in the direction of the collection return 120.

The water or other aqueous liquid may flow downward over the material drape 110 and through one side or both sides of the material drape 110, including a wicking effect for upward and downward flows while allowing ambient air to pass through. It should be noted that if a laminar flow of water or other aqueous liquid over the surfaces of the material drape 110 is created or controlled by the speed or velocity of pump 240, evaporation will occur, but the excess moisture while slightly restricting or controlling air movement will have the added benefit of "scrubbing" the air as it moves through the flowing water. This benefit may reduce pollutants, allergens, insects and the like. The gutter 255 may be filled manually without the use of pump 240 in some embodiments (not shown). The collection return 120 may either be independent or attached to a recirculation system as shown. The inline filter 135 may remove contaminants picked up during the movement of the water or other aqueous liquid.

An ionizing element (not shown) may be incorporated inline to create pH changes in the water or other aqueous liquid for sterilizing purposes.

The drape 110 may be mounted for vertical or horizontal movement or retraction or mounted in a fixed manner. If vertically mounted, the drape 110 may roll to the side or fold when not being utilized. If horizontally mounted as shown in FIG. 1, the drape 110 may roll or fold upward or downward with respect to the horizontal.

The drape assembly 100 may include an inline heating element (not shown) to increase the temperature of the water or other aqueous liquid.

Figure 3:
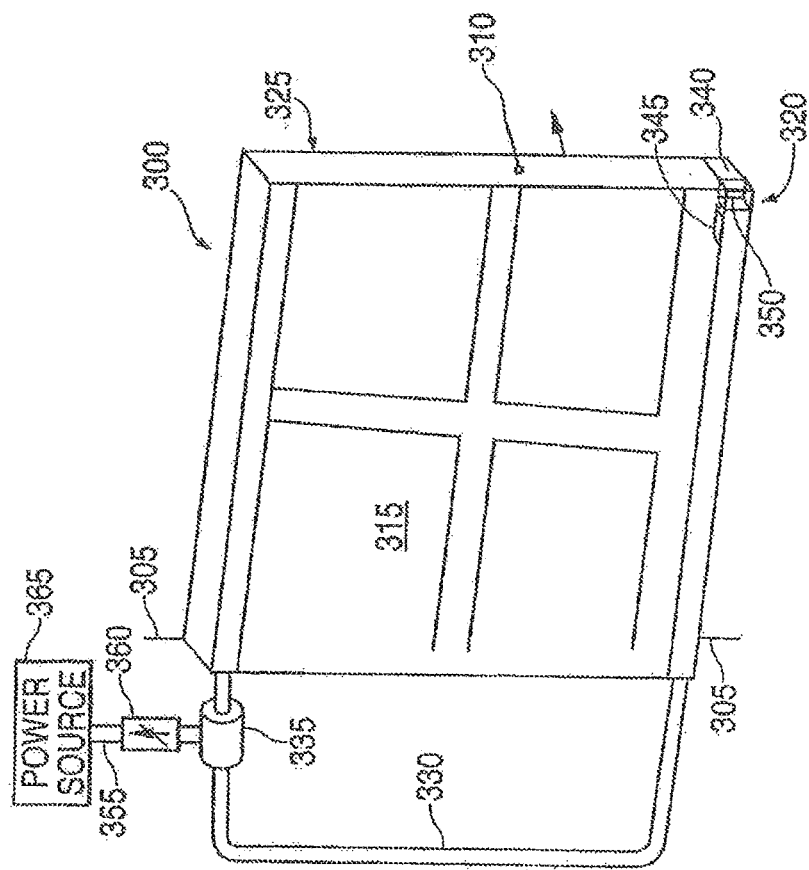
FIG. 3 is a perspective view in accordance with an embodiment of the invention.

Referring to FIG. 3, an embodiment of the present inventive apparatus and method provides a pivotal window drape assembly 300 having pivot hinges 305, a latch 310, a fixed screen drape material 315, a drain opening 320, mounting frame 325, tubing 330, a high volume pump 335, collection tray 340, collection tray float 345, overflow float valve 350, solenoid reservoir drain 355, a pump power line 360, an on/off switch 365 to a power source 370 which preferably is a GFCI power line.

In this embodiment the window drape assembly 300 opens inwards within a building or structure and utilizes a high volume pump 335 to create a waterfall effect upon the fixed screen material 315. This waterfall effect provides for a degree of privacy as well as a measurable amount of humidity to interior spaces as air may be allowed to pass.

Figure 4:
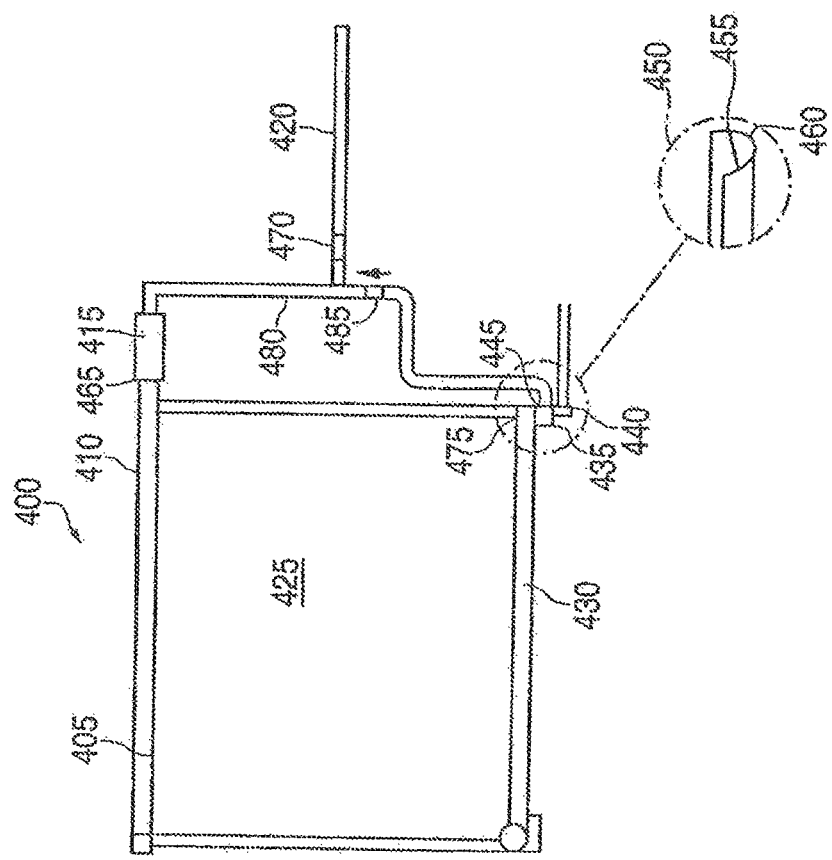
FIG. 4 is a diagrammatic representation in accordance with an embodiment of the invention.

Referring to FIG. 4, an embodiment of the present inventive apparatus and method provides a walled drape assembly 400 having a slit 405; a gutter 410; a pump 415; a water main 420; a material drape 425; a reservoir/catch basin 430 having sidewalls 450, drainage openings 460 and an overflow level indicator 455; a float 435; a catch basin solenoid drain 440; a catch basin overflow region 445; a swivel pump connector 465; a water main solenoid 470; a pump contact switch 475; a feed line 480; and a one-way valve 485.

The walled drape assembly 400 is configured to be set back into a wall. The swivel connector 465 allows for some flexibility in setting the assembly 400 into a well as desired. The contact switch 475 turns on the pump 415 either manually or remotely as desired. The water main 420 provides water or other aqueous liquid to the pump 415 and is controlled by solenoid 470. The catch basin 430 retrieves and circulates the water or other aqueous liquid via the feed line 480. There is a one-way valve disposed inline with the feed line 480 to prevent backflow to the catch basin 430. The catch basin 430 utilizes a solenoid drain 440 in combination with float 435 to sense and prevent overflow conditions of the basin 430. The gutter 410 receives the liquid from pump 415 and the liquid subsequently flows from slit 405 onto drape 425 accordingly. The drape 425 may be retractable by use of an elastic spring or stock spring or both (not shown) depending on the size and length of the drape 425 used. A manually operated embodiment has no pump but may use a seeper hose which moistens the drape 425 and then fills the catch basin 430. However, the catch basin 430 may overflow and therefore requires manual draining via drain 440.

Figure 5:
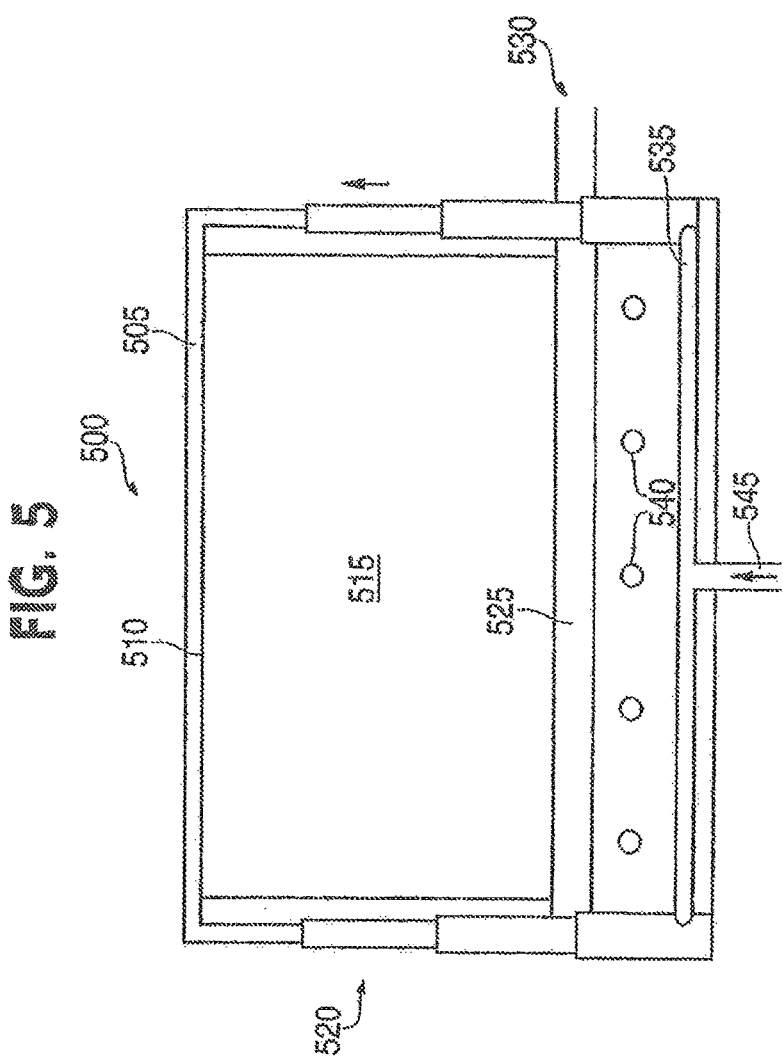
FIG. 5 is a diagrammatic representation of an embodiment of the invention.

Referring to FIG. 5, an embodiment of the present inventive apparatus and method provides a water curtain assembly 500 having a water gutter 505, a water drainage slit 510, a material drape 515, hydraulic telescopic piston sleeves 520, a drape storage cavity 525, a water inlet 535, a plurality of return drains 540, and a diverter pump or dedicated pump 545 as desired.

The connection between the water gutter 505 and the piston sleeves 520 may be configured at a ninety degree angle thereby reducing the flow of water or other aqueous liquid to gutter 505 and subsequently to slit 510. This embodiment may be applicable to hot tubs and the like. A diverter pump or dedicated pump 545 may provide pressurized water for a hot tub or other primary source 530 to piston sleeves 520 thereby causing the sleeves 520 to expand telescopically from an initial position to a desired height or length. As the piston sleeves 520 expand, the drape 515 may freely unravel and move upward with the sleeves 520. The water or other aqueous liquid will propagate within the sleeves 520 into the gutter 505 and out the slit 510 upon the drape 515 creating a water curtain effect. When the water pressure from the pump lessens or ceases the piston sleeves 520 will lower and return to the initial position and the drape 515 will reside and be disposed within storage cavity 525 accordingly. The water or other aqueous liquid propagating down the drape 515 may be recycled through a plurality of return drains 540 back to the hot tub or primary source 530.

Although an example of the water curtain is shown using a fiber glass mesh drape, it will be appreciated that other structured materials can be used. Also, although the water curtain is useful to increase humidity in the air flow it can also be used to create insect barriers, sound baffling or barriers, privacy screens or fences, reflect indirect light, grab dust or allergens, perform active cooling with forced air flows, and/or passive cooling with air flows alone.

Figure 6:
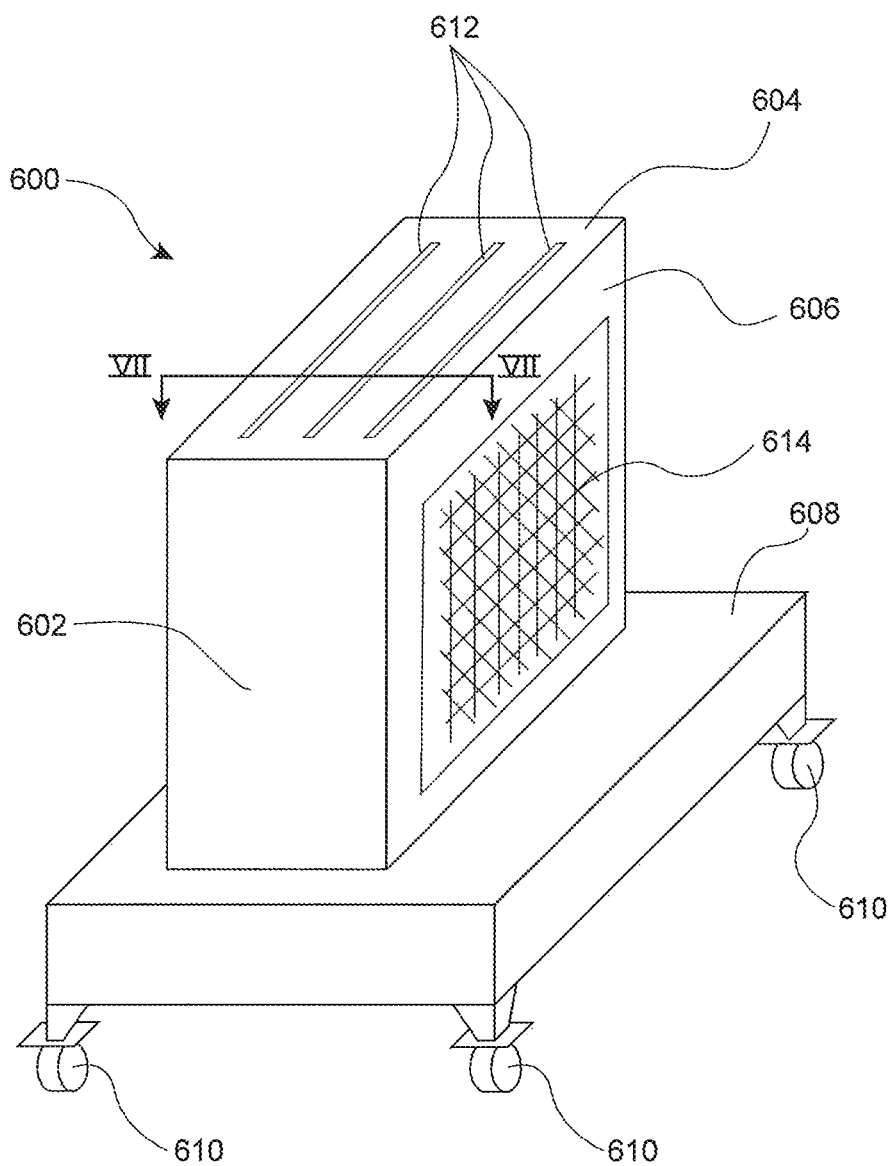
FIG. 6 is an illustrative embodiment of an evaporative cooler according to the present invention.

An illustrative embodiment of an active evaporative cooler and air purifier is shown in FIG. 6. The evaporative cooler 600 can include a housing 602 having an upper surface 604 and at least one vertical wall 606 defining an interior chamber (not shown). In addition, the evaporative cooler 600 can include a base 608 for supporting the housing 602. The base 608 can be configured with casters 610 or any other device so as to permit the evaporative cooler 600 to be easily mobile for transport from location to location. The evaporative cooler 600 can be disposed outdoors, for example to cool a patio area, or the cooler 600 can be mounted in a window or entryway for outdoor to indoor evaporative cooling of a building or enclosure. The evaporative cooler can further include the electrical circuitry and piping previously described to provide the power, safety and drainage features described in connection with the previous embodiments.

The evaporative cooler 600 can be generally configured for active cooling in which the surrounding ambient air can be forced drawn into and expelled from the housing 602. Accordingly, the upper surface 604 can include one or more slots or vents 612 through which ambient or surrounding air can be drawn into the inner chamber of the housing 602. Vents 612 are shown as running in the longitudinal direction of the housing 602, but other configurations are possible such as, for example, running in the transverse direction of housing 602 or being located on a vertical wall 606 of the housing 602. The air drawn into the housing 602 can be filtered, humidified and cooled by being passed through a material drape or screening element 614 disposed along a vertical wall 606 of the housing 602 with a fluid layer flowing over the surface of the screening element 614. The screening element 614 can be disposed within vertical wall 606 so as to be framed in a portion of the vertical wall 606 or alternatively, the screen element can be secured within the framework of the housing 602 such that the screen 614 substantially forms the vertical wall 606 in its entirety. The screen 614 can be further disposed so as to be substantially parallel to the vertical wall 606 or alternatively, the screen 614 can be positioned so as to be at an angle relative to the vertical wall 606. As is described in greater detail below, the screening element 614 can be coupled to a drain assembly such that a fluid can be moved over the screen 614 so as to filter, humidify and/or cool the air passing through the screening element 614.

The housing 602 is shown as being substantially block rectangular or prism-like in shape. Accordingly, the housing 602 shown in FIG. 6 includes four supporting vertical walls 606. In one embodiment of the evaporative cooler 600, the vertical walls 606 defining the elongate sides of the housing 602 can be configured with a screen 614 so as to form parallel evaporative cooling screens. Alternatively, only one of the parallel screens 614 can be configured for evaporative cooling in which the fluid layer is conveyed over the one screen. The other of the parallel screen element 614 can be configured to act as a drape, shield or barrier to minimize or reduce the scatter of fluid around and/or external to the housing 602 that may be dispersed by air moving over the one evaporative cooling screen. Further, each vertical wall 606 of the evaporative cooler 600 can include a screen 614 or further in the alternative, a single vertical wall 606 can include a screening element 614. Generally, the evaporative cooler 600 can be fitted with as many screens 614 as can be effectively coupled to or in communication with the drain assemblies of the evaporative cooler 600 so as to provide the evaporative cooling and filtering effects as described below.

Figure 7:
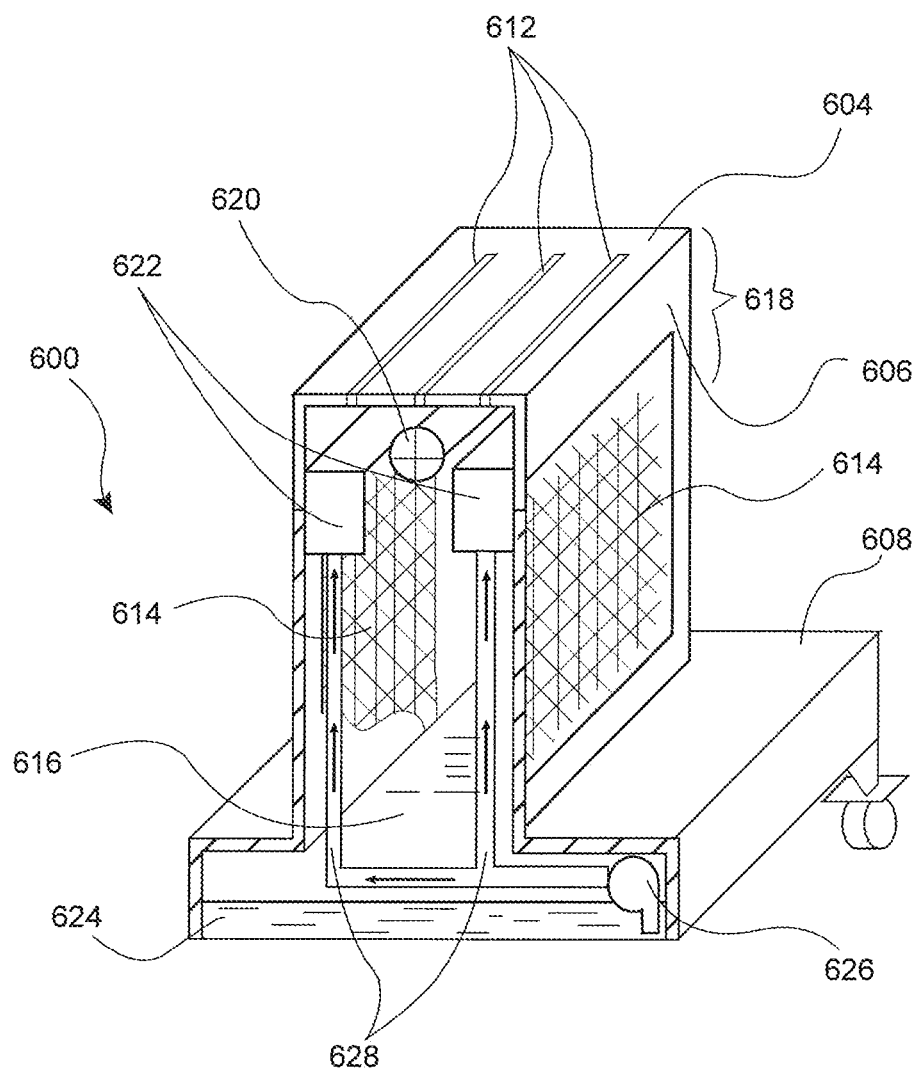
FIG. 7 is a cross-sectional view of the evaporative cooler of FIG. 6 cut along line VII-VII.

Shown in FIG. 7 is a cross-sectional view of the evaporative cooler 600 in which the upper surface 604 and the vertical walls 606 can define an interior chamber 616. Each of the parallel elongate vertical walls 606 of the housing 602 has a screening element 614. The screening element 614 defines an interior surface and an exterior surface relative to the interior chamber 616. The screening element 614 can be configured as a single layer element. Moreover, the screening element 614 can be constructed by weaving, pressing or other forming process so as to form the single layer element.

The screening element 614 can be further constructed and disposed within the housing 602 so as to permit air to flow from the interior chamber 616 to the outer environment. The screening element 614 can define a mesh opening size so as to provide an airflow suitable for a given application of cooler 600. For example, the screen 614 can include a mesh opening ranging from about 1/64 inch to about 3/8 inch, although other mesh sizes are possible, as required to produce the desired evaporative cooling effect and fluid flow characteristics for air passing through and fluid flowing over the screen element 614. More specifically, the mesh size of the screen element 614 can be configured so as to alter the pressure or air volume requirements of the cooler 600. For example, where the mesh size of the screen element is 1/4 inch, the cooler 600 may not need a large air conveyor to move air through the screens 614 as compared to a cooler 600 configured with a screen element 614 having a smaller mesh size. In addition, the mesh openings of the screen element 614 can be sized and configured so as to effect the fluid flowing over the screen 614. The screen element 614 can be generally configured such that fluid dispensed over the screen 614 forms a two-dimensional or surface fluid layer. Where the screen element 614 is configured as a single layer element and fluid flow is restricted to the surface of the screen 614, the wet bulb temperature of the ambient air can be optimized or maintained over a longer period of time so as to deliver sustained evaporative cooling of the air. In addition, the screen 614 can be configured such that fluid flowing over the screen 614 defines a decorative pattern that can be aesthetically pleasing. Moreover, the screen 614 can be constructed from a translucent material such that, in combination with the transparent/translucent fluid layer flowing over the screen 614, a translucent barrier can be defined to provide privacy and adequate lighting to an area framed or fenced by the evaporative cooler 600. To facilitate the visual effects provided by the screen 614 and the fluid flowing thereover, the housing can be constructed from translucent material.

The upper portion of the housing 602 can define a hood basin area 618. The hood basin area 618 can include an air conveyor 620 disposed and configured for drawing air into the chamber 616 through vents 612. The air conveyor 620 can be, for example, a fan or similar device configured to rotate about an axis substantially parallel to the longitudinal axis of the housing 602. The air conveyor 620 can provide the force for expelling the air from the chamber 616 alongside and/or through the screening elements 614. In this manner, the air conveyor may be configured to generate a mingling of particles. Moreover, the air conveyor 620 can provide the positive pressure within the chamber 616 such that air moving through the evaporator 600 moves from the inner chamber 616 to the outer environment. Where the screen 614 has been configured so as to minimize the size requirements of the air conveyor 620, the noise generated by the air conveyor 620 can be minimized or reduced so as not to disrupt the surrounding environment.

The hood area 618 can further provide an area from which the screening elements 614 can be supported and coupled to or in communication with drain slit assemblies 622. Drain slit assemblies 622 can be configured and disposed relative to the screens 614 to provide a controlled flow of fluid such as, for example, water over the screens 614. The drain slit assemblies 622 can be configured, for example, in a manner substantially similar to the piston sleeve and gutter assembly of FIG. 2B. Accordingly, each of the drain slit assemblies 622 can be coupled to or disposed relative to a screen element 614 so as to deposit a fluid film or surface fluid layer over the screen 614. The screen 614 can be coupled to or in communication with the drain slit assembly 622 such that the fluid film can be deposited on either the interior or exterior surface of the screen 614, or alternatively on both the interior and exterior surfaces of the screen 614 so as to define the surface fluid layer. In addition, the drain slit assembly 622 can be configured and coupled or disposed relative to the screen element 614 such that the fluid layer has a continuous laminar flow over the screening element 614. Thus air passing through the vents 612 of the evaporative cooler 600 can be conveyed through the screen elements 614 and the flowing fluid layer so as to be filtered and humidified for delivery into the external environment. The fluid layer flowing over the screen elements 614 can be collected in a re-circulating pool 624 formed within the base 608. The screen 614 is shown in-part in FIG. 7 for ease of viewing to illustrate that the screen elements 614 can be configured so as to extend into the re-circulating pool 624 thereby minimizing spill over or splashing of the fluid outside of the housing 602. A pumping device 626 can further be disposed within the base 608 to circulate the collected fluid back to the drain slit assemblies 622 through fluid return piping 628. Alternatively, the cooling unit 600 can derive its fluid source externally. More specifically, the cooling unit 600 can be disposed within, for example, a pool of water, with the base 608 and pumping device in communication with the pool of water to deliver the fluid to the drain slit assemblies 622.

Figure 8:
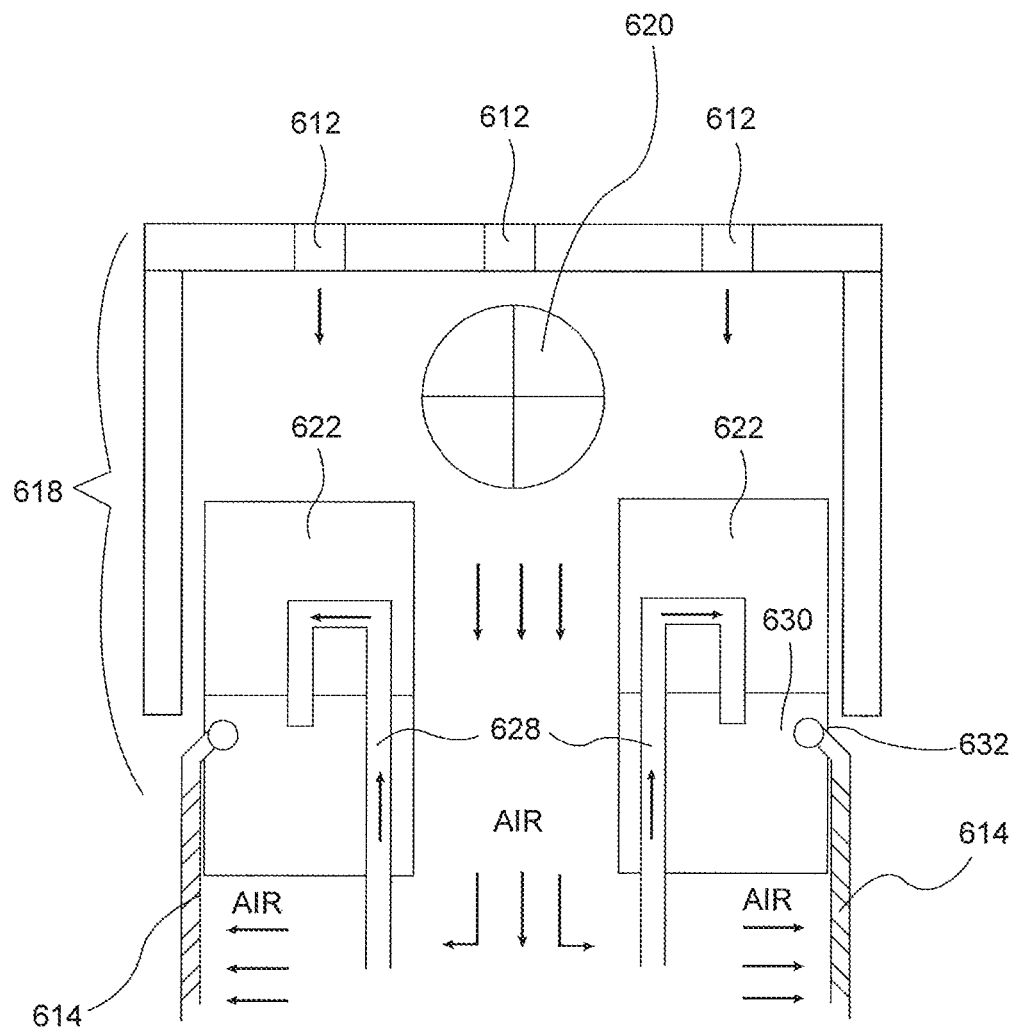
FIG. 8 is an illustrative embodiment of the hood basin area in the evaporative cooler of FIG. 6.

Shown in FIG. 8 is an illustrative embodiment of the hood area 618. More specifically shown are the drain assemblies 622 coupled to or disposed relative to the screen elements 614 for distributing fluid over the screen 614. Each drain assembly 622 can include return piping 628 feeding circulated fluid from the re-circulating pool 624 into the fluid holding area 630 of the drain slit assembly 622. The drain slit assembly 622 can include a slit 632 configured to secure the screen element 614 and through which fluid can flow onto the screen element 614. Alternatively, the screen 614 can be secured to a portion of the hood area 618 and spaced relative to the drain slit assembly 622 such that fluid can be discharged from the slit 632 and dispersed over the screen 614. The rate of the fluid flow over the screen element 614 can be controlled by, for example as earlier described, the velocity of the pumping mechanism 626. Alternatively, the drain slit assembly 622 can include a pump independent of pumping mechanism 626 to deliver and control the fluid flow over the screen element 614. Further in the alternative, the flow characteristics of the fluid layer over the screening element 614 can depend upon the head pressure of fluid above the slit 632 and the geometry of the slit 632. Schematically shown in FIG. 8 is the air flow through the hood portion 618 of the evaporative cooler 600.

Figure 9:
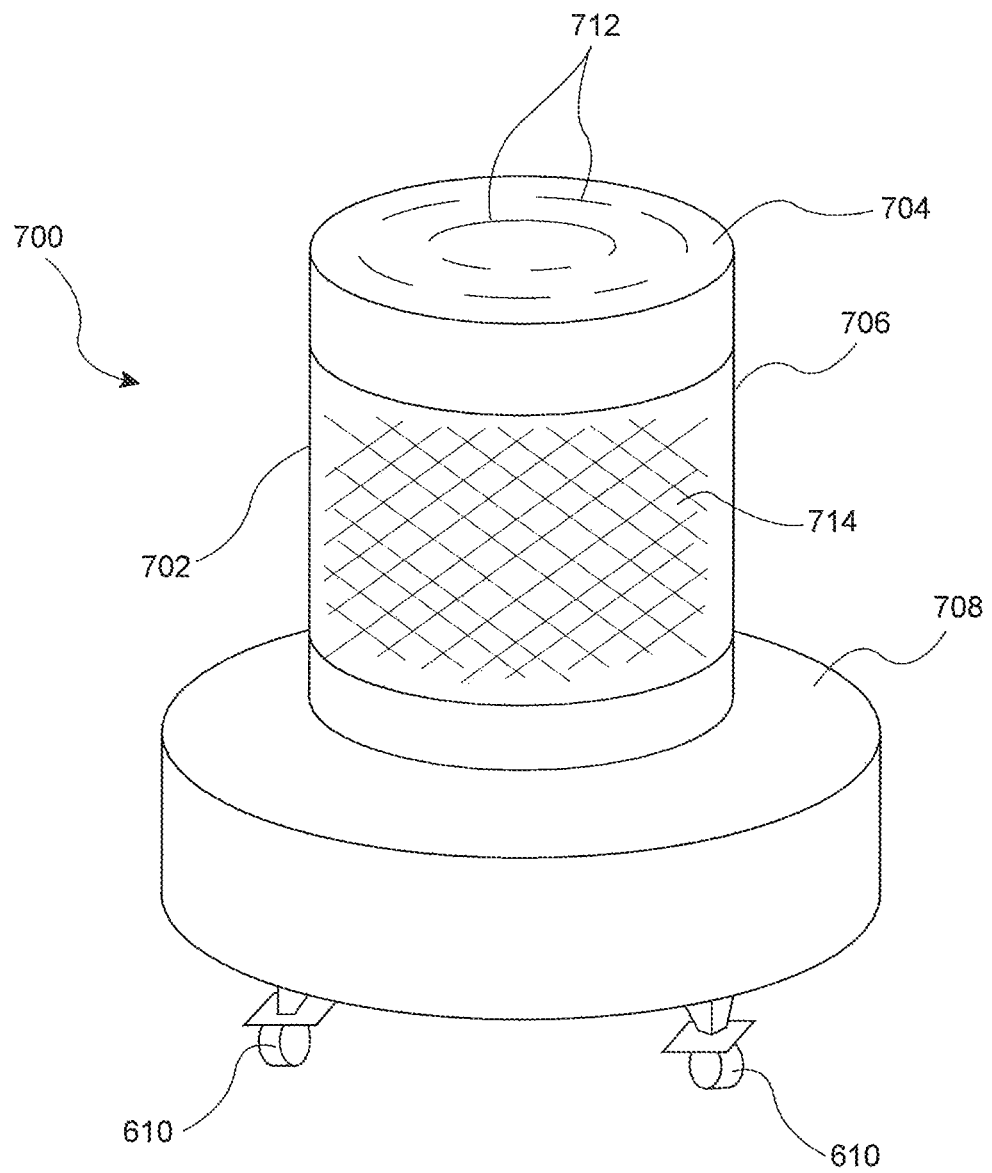
FIG. 9 is another illustrative embodiment of an evaporative cooler according to the present invention.

The housing and the base of the evaporative cooler and air purifier can be any geometry, for example, circular cylindrical as is shown in FIG. 9. FIG. 9 shows an alternative illustrative embodiment of the evaporative cooler 700 having both a housing 702 substantially circular cylindrical in shape. The housing 702 can include an upper surface 704 and a vertical or side wall 706 defining an interior chamber (not shown). The upper surface 704 of the evaporative cooler 700 can include one or more vents 712 through which the outside air can pass into the interior chamber for active or passive cooling. The vents 712 are shown as concentric arcs spaced about the upper surface 704, but the vents 712 can be disposed about the upper surface 704 in other formations. The vertical wall 706 defining the cylindrical shape of the housing 702 can be formed substantially by the material drape or screening material 714. Fluid can be distributed over the screen 714 for filtration and/or evaporative cooling of the air drawn into the interior chamber. Alternatively, the vertical wall 706 can include a series of spaced apart windows for framing two or more screens 714. The screen 714 can be disposed so as to be substantially parallel to the vertical wall 706 or alternatively, the screen 714 can be positioned so as to be at an angle relative to the vertical wall 706. Moreover, the screen 714 can be constructed and configured in a manner substantially similar to screen element 614 so as to have substantially similar fluid flow characteristics and light transmitting effects. More specifically, screen 714 can be configured such that fluid flowing over the screen 714 forms a two-dimensional or surface fluid layer over the screen 714. The evaporative cooler 700 can further include a base 708. The base 708 can include casters 610 or similar device to make the evaporative cooler 700 mobile.

Figure 10:
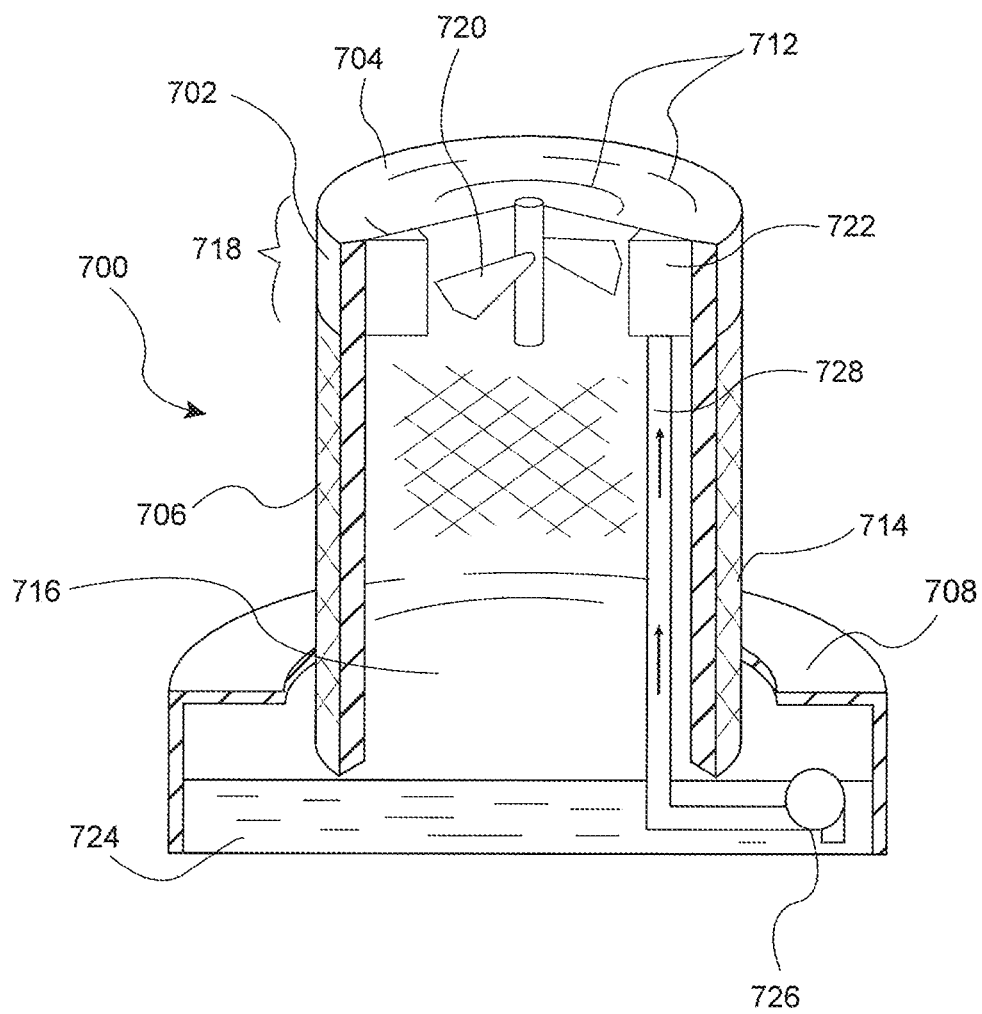
FIG. 10 is a cross-sectional view of the evaporative cooler of FIG. 9.

Shown in FIG. 10 is a cross-sectional view of the evaporative cooler 700 in which the upper surface 704 and the vertical walls 706 define an interior chamber 716. The screening element 714 disposed along the vertical wall 706 can define an interior surface and an exterior surface relative to the interior chamber 716. The upper portion of the housing 702 can house the hood basin area 718. The hood basin area 718 can include an air conveyor 720 disposed and configured for drawing air into the chamber 716 through the vents 712 for active cooling. The air conveyor 720 can be, for example, a fan or similar device configured to rotate about the central or longitudinal axis of the housing 702. The air conveyor 720 can provide the force for expelling the air from the chamber 716 through the screening elements 714. Moreover, the air conveyor 720 can provide the positive pressure within the chamber 716 such that moving air moving through the evaporator 700 moves from the inner chamber 716 to the outer environment.

The hood area 718 can further provide an area from which the screening elements 714 can be supported and coupled or disposed relative to a drain slit assembly 722. The drain slit assembly 722 can be configured to provide a controlled flow of fluid such as, for example, water over the interior surface, exterior surface or both of screen 714 so as to provide filtration, humidification and/or cooling of the drawn in air. The drain slit assembly 722 can be further configured such that the fluid film has a laminar flow over the screening element 714. The drain slit assembly 722 can be configured in a manner substantially similar to the drain slit assembly 622 and further configured as a continuous ring circumscribed by the hood basin area 718. Alternatively, the drain slit assembly can be a series of spaced apart segmented ring portions to provide the fluid flow. The screen 714 can be coupled to or disposed relative to the drain assembly 722 in a manner as previously described regarding the screen 614 and the drain slit assemblies 622 of the evaporator 600. Although not shown, with the evaporative screen 714 having a fluid layer disposed thereover, a secondary screen can be provided to parallel or circumscribe the screen 714 to act as a shield or barrier to minimize or reduce the scatter of fluid around and/or external to the housing 702 that may be dispersed by air moving over the evaporative cooling screen 714.

The base 708 of the evaporative cooler 700 can include a re-circulating pool 724 for catching and re-circulating fluid moved over the screening elements 714. A pumping device 726 can further be disposed within the base 708 to circulate the collected fluid back to the drain slit assembly 722 through the return piping 728. Alternatively, the cooling unit 700 can derive its fluid source externally. More specifically, the cooling unit 700 can be disposed within, for example, a pool of water, with the base 708 and pumping device 726 in communication with the pool of water to deliver the fluid to the drain slit assemblies 722. The screen 714 can be disposed and configured so as to be spaced from the base 708 and extended into the re-circulating pool 724 thereby minimizing spill over or splashing of the fluid outside of the housing 702.

Figure 11:
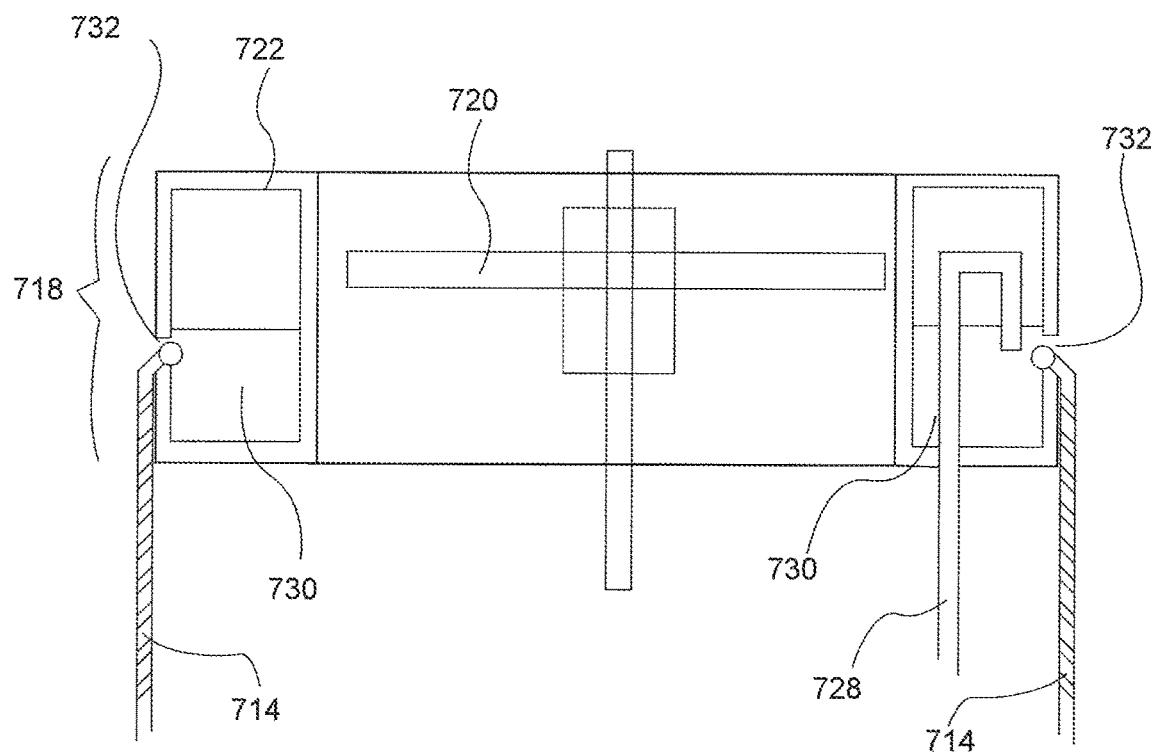
FIG. 11 is an illustrative embodiment of the hood basin area in the evaporative cooler of FIG. 9.

Shown in FIG. 11 is an illustrative embodiment of the hood area 718. More specifically shown is the drain slit assembly 722 coupled to the screen element 714. The drain slit assembly 722 can include return piping 728 feeding circulated fluid from the re-circulating pool 724 into the fluid holding area 730 of the drain slit assembly 722. The drain slit assembly 722 can include a slit 732 configured to secure the screen element 714 and through which the fluid can flow onto the screen element 714 in a layer having laminar flow. The rate of the fluid flow over the screening element 714 can be controlled by, for example as previously described, the velocity of the pumping mechanism 726. Alternatively, the drain slit assembly 722 can include a pump independent of the pumping mechanism 726 to deliver and control the fluid flow over the screening element 714. Further in the alternative, the flow characteristics of the fluid layer over the screening element 714 can depend upon the head pressure of the fluid above the slit 732 and the geometry of the slit 732.

Figure 12:
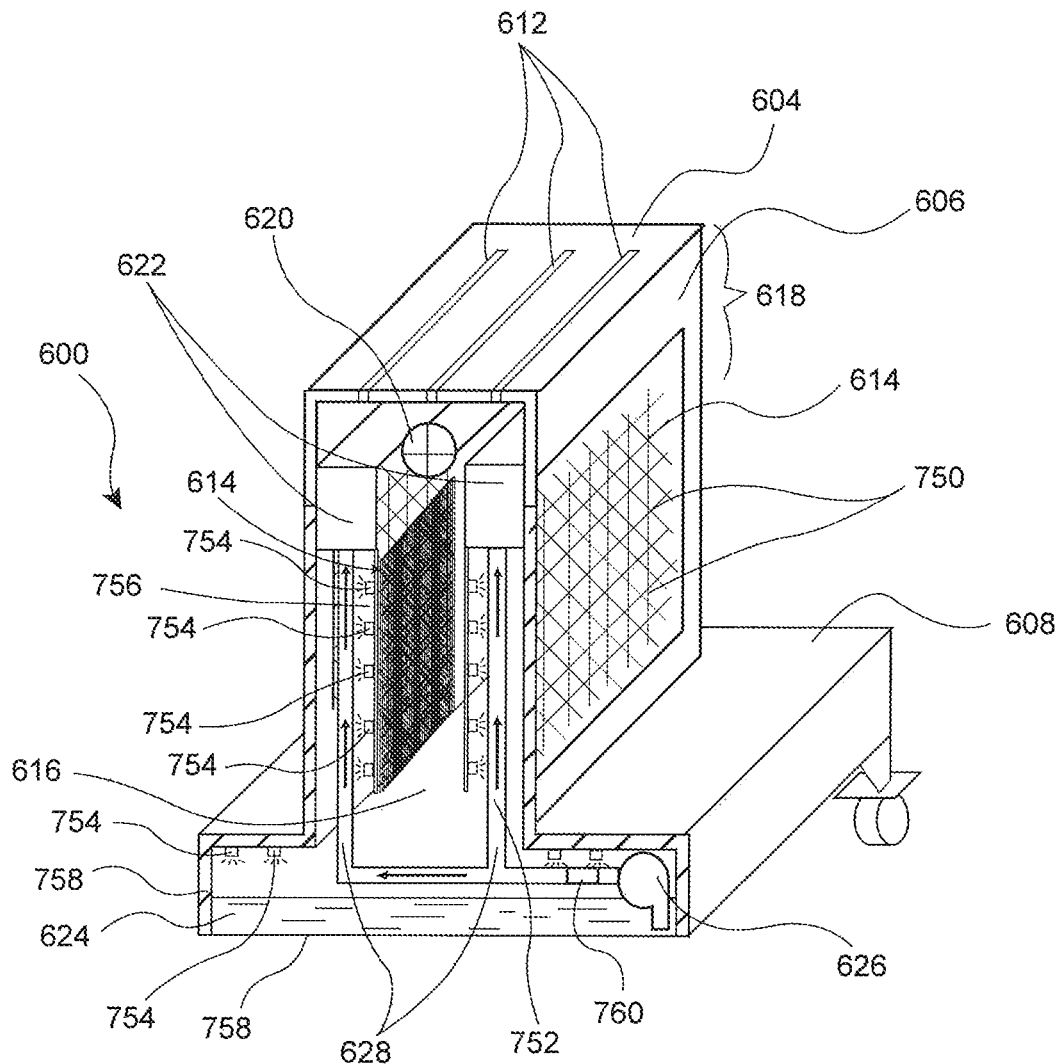
FIG. 12 is a cross-sectional view of another embodiment of the evaporative cooler of FIG. 6 having self-cleaning components cut along line VII-VII of FIG. 6.
Figure 13:
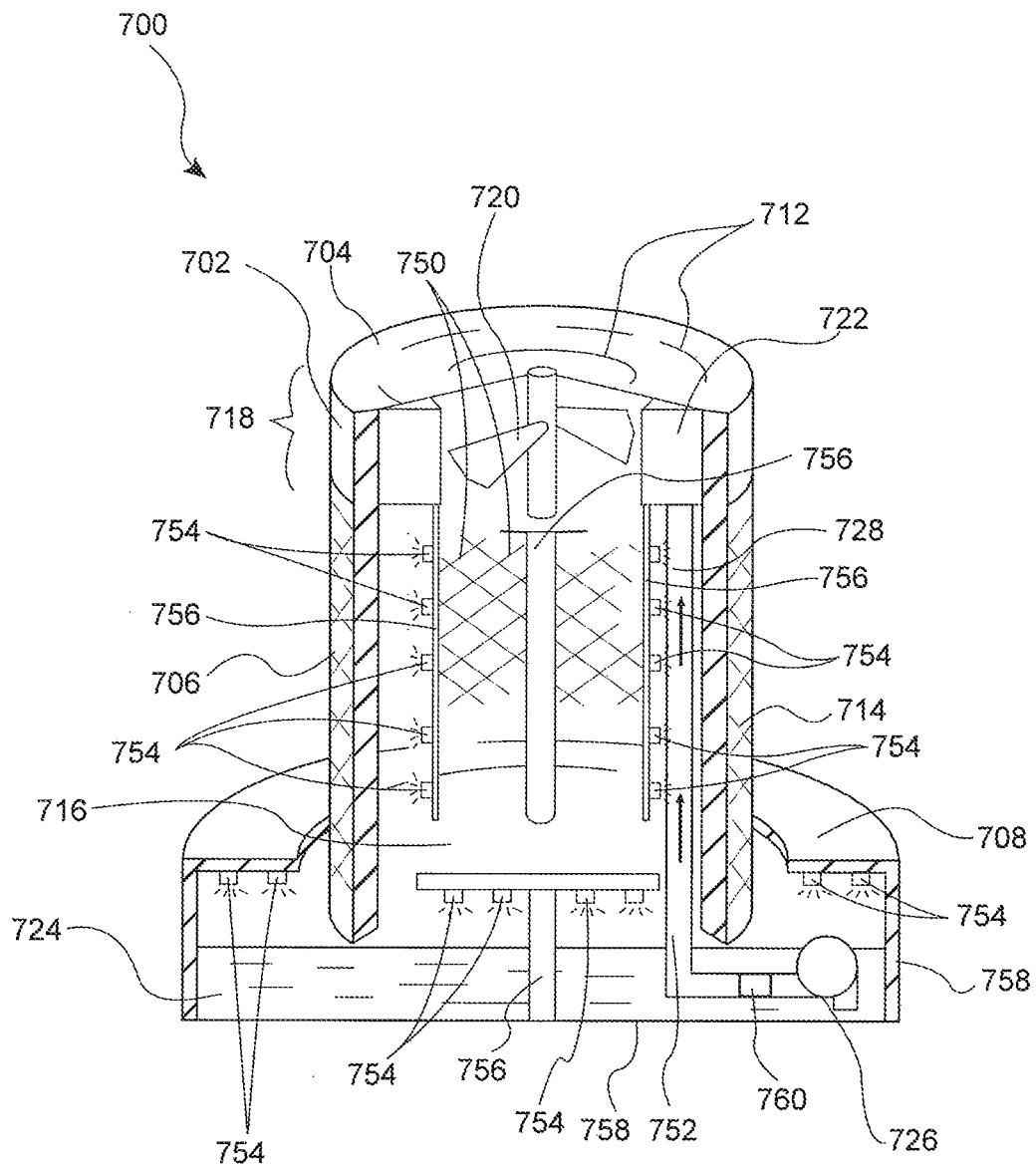
FIG. 13 is a cross-sectional view of another embodiment of the evaporative cooler of FIG. 9 having self-cleaning components.

Some additional embodiments of the cooler 600 and 700 are illustrated in FIGS. 12 and 13. The embodiments illustrated in FIGS. 12 and 13 are similar to the embodiment illustrated in FIGS. 6 and 7 and the embodiment of FIGS. 9 and 10 respectively. Common features to the embodiments which were previously described above will not be repeated here for the sake of brevity.

The embodiments illustrated in FIGS. 12 and 13 contain additional components to provide self-cleaning and self-purifying of the water and/or coolant used in the coolers 600 and 700 as well as purifying the air that is moved through the coolers 600 and 700. The additional components may help to remove, kill, and/or render inert contaminants and/or pathogens such as, but not limited to: bio-fouling such as microorganisms, bacteria, algae, parasites, bacteria, viruses, and fungi. In some embodiments, the additional components may render the water and/or fluid used with in the cooler 600 and 700 to be bio static and, in some embodiments the additional components may be corrosion resistant.

As can be appreciated by one of ordinary skill the art, air, even indoor air that is been treated with that HVAC system can contain undesired particulate matter, dust, dirt, pet dander, hair, fur, biological matter, microbial matter and other undesired matter. The embodiments illustrated in FIGS. 12 and 13 provide additional components that allow the various undesirable matter to be removed from the air to the coolant and/or water flowing down the screen 614, 714 and then have the various undesirable matter rendered inert and/or removed from the fluid or water.

For example, when air moves through the screens 614, 714 as described above, the various undesired matter can be captured by the water and/or coolant flowing through the screens 614, 714 and removed from the air. As a result, the air that moves out of the cooler 600 and 700 is purified. As described above, in some embodiments, the water and/or coolant is recirculated through the cooler 600 and 700. As a result, it may be desired to purify the water and/or coolant used to clean the air.

If the water and/or coolant contained in the cooler 600 and 700 is not cleaned, undesired biological growth in the water and/or coolant, or buildup of other undesirable matter may occur at various points along the cooler 600 and 700. In addition, the water and/or coolant can become dirty and, as a result, become unsightly and, in addition to lose or have reduced ability to remove foreign matter out of the air.

As shown in FIGS. 12 and 13, in order to reduce the amount of undesired substances in the water, a filter assembly 760 may be located along the conduit 752 that is used to recirculate the cooling fluid or water. The filter assembly 760 may be configured to remove various particulate and other contaminants within the water cooling fluid with a conventional filter arrangement.

In addition to, or in some instances instead of, the filter assembly 760, the cooler 600 and 700 may be at equipped with other water cleaning or purification components. For example, in some embodiments antimicrobial metals such as copper, Muntz metal, copper-zinc alloys, copper-nickel alloys, copper silicon alloys, other copper alloys, silver, copper with silver plating or other antimicrobial metals or other antimicrobial materials may be used. The antimicrobial metals may be located at various locations around the cooler 600 and 700 in order to kill or render inert microbes, microorganisms, bacteria, algae, parasites, viruses, fungi and/or any other undesired things contained in the water or cooling fluid.

For example, the screen 614, 714 may be made of weaved metal strands 750 which are antimicrobial metals. As a result, when the water and/or cooling fluid flows down the screens 614, 714 microbes or other living matter captured from the air and not trapped in the water and/or cooling fluid may be killed or rendered inert.

In addition to, or instead of, screens 614, 714 being made of antimicrobial metals, the recirculating conduit 752 and the recirculating pool 624, 724 (sometimes referred to as a catch basin) may have walls 758 made of antimicrobial metals. As result, as the water or cooling fluid resides in the recirculating pool 624, 724 the water or cooling fluid may contact the antimicrobial walls 758 which will kill or render inert microbes or other undesirable substances in the fluid or water.

Optionally, in some embodiments, the cooler 600, 700 may be equipped with lights 754. The lights 754 may emit ultraviolet light which can, in some instances, kill or render inert various bio-matter. In some embodiments, the lights 754 are light emitting diodes (LED) lights. In some embodiments, the lights 754 are mounted to light mounts 756 which orient the lights 754 to shine on the cooling fluid and/or water contained in the recirculating pool (reservoir, or catch basin) 624, 724 or even the conduit 752. In some embodiments, the light mounts 756 may also provide appropriate control circuits and electrical power to operate the lights 754.

In some embodiments, the LED lights 754 may be oriented to illuminate shine on the water and/or cooling fluid flowing through the screens 614, 714. The LED lights 754 may be colored and be capable of shining various colors in order to provide a pleasing aesthetic quality to the cooler 600, 700.

The particular orientations illustrated in FIGS. 12 and 13 are for illustrative purposes only. One of ordinary skill the art after reviewing this disclosure will understand how to orient the lights 754 in order to illuminate and kill and/or render inert bio-matter contained in the cooling fluid or water.

In addition to using copper alloys, silver or other substances for clearing cleaning the water or cooling fluid, some embodiments may also incorporate chemicals in the water cooling fluid. For example bleach or chlorine may be mixed in with the water cleaning fluid in order to render the water cleaning fluid more bio static and/or pure. Other chemicals or substances may also be used in accordance with various embodiments which are known to clean and/or purify fluids and/or water.

Figure 14:
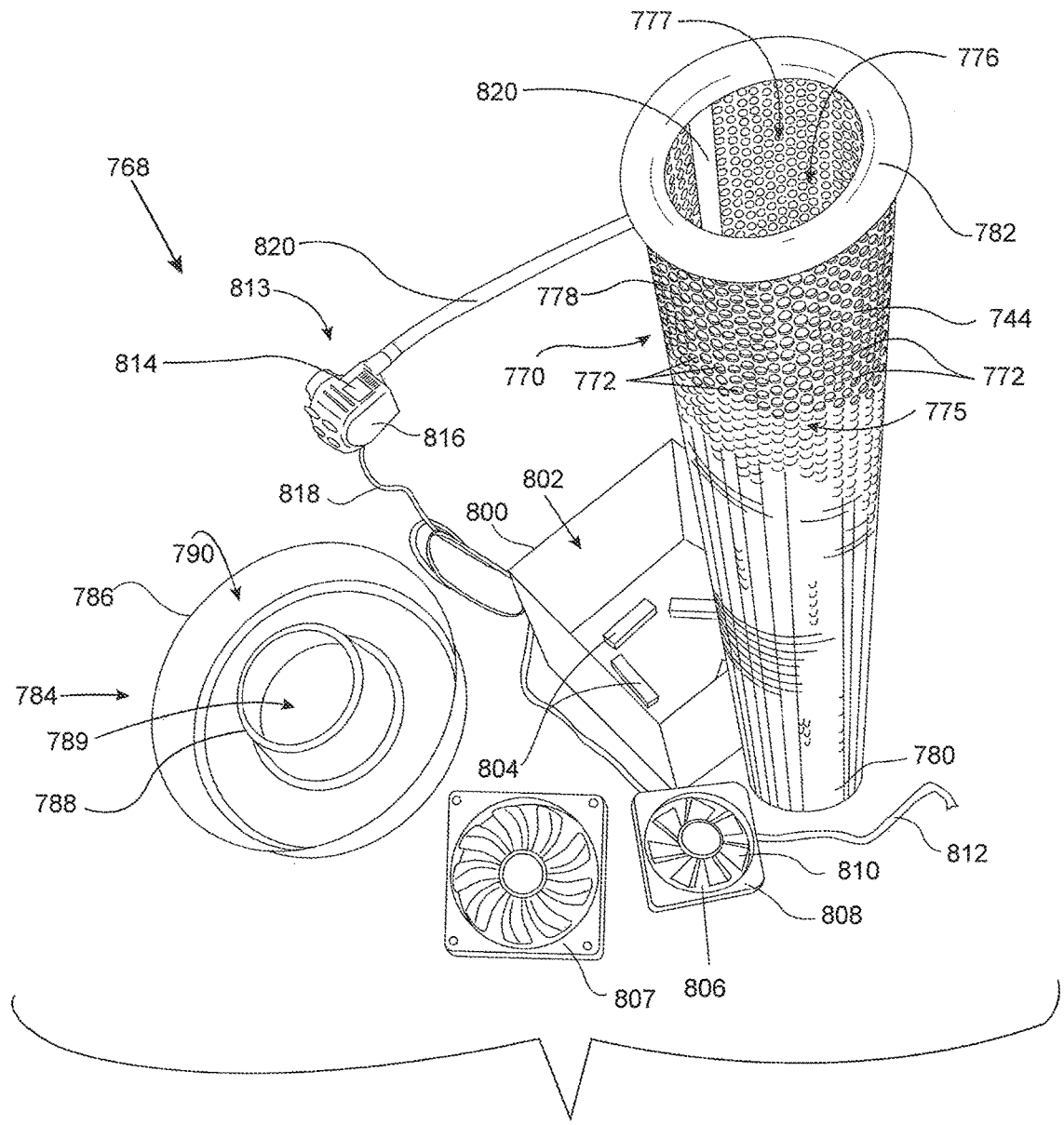
FIG. 14 is an exploded view of an air purifier in accordance with another embodiment.
Figure 15:
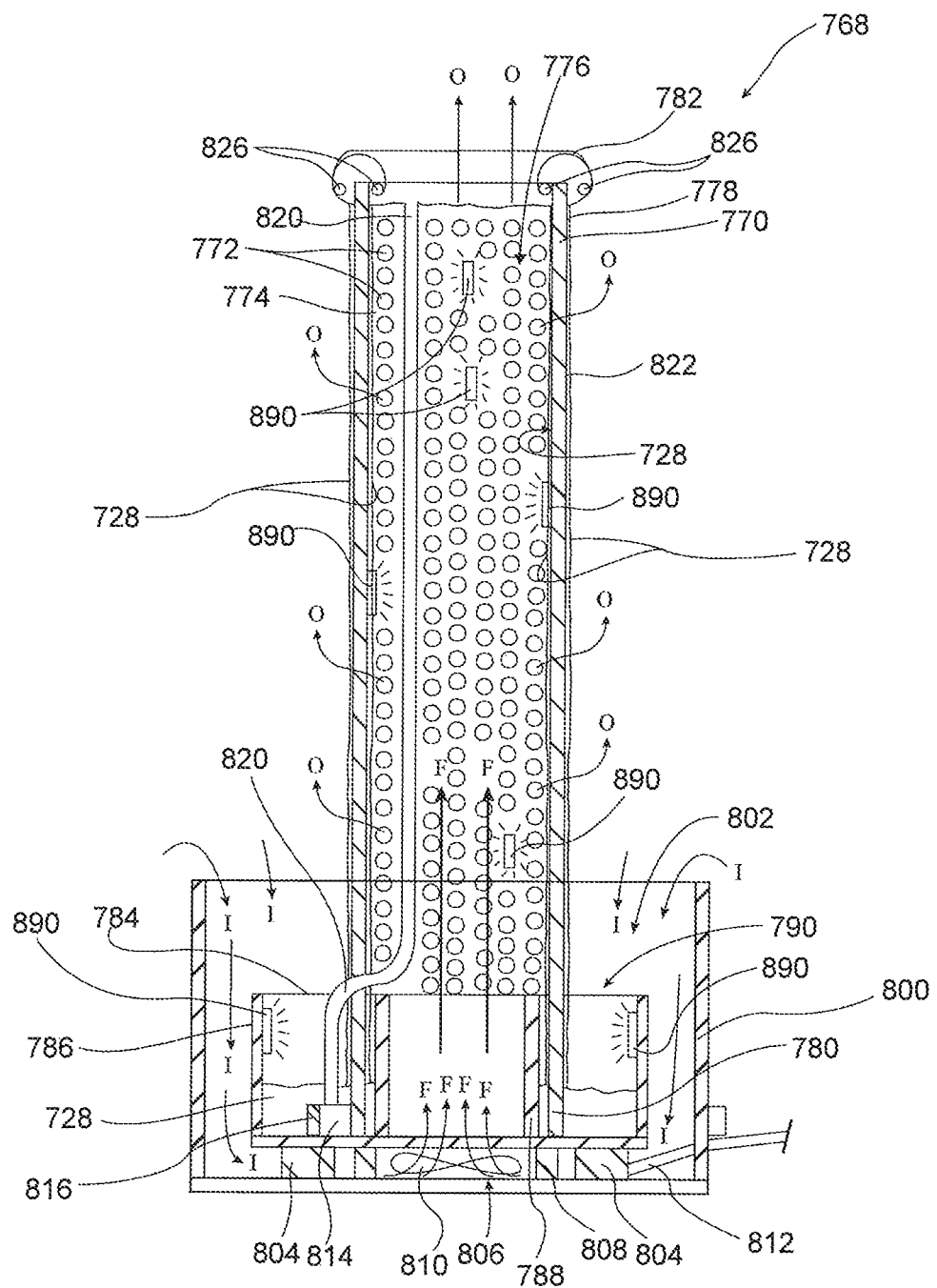
FIG. 15 is a cross-sectional view of the air purifier shown in FIG. 14.

FIGS. 14 and 15 illustrate another embodiment in accordance with the present disclosure. FIG. 14 is an exploded view of an air purifier 768 in accordance with another embodiment. FIG. 15 is a cross-section assembled view. The two figures will be described together. The air purifier 768 includes a perforated tube 770. While the perforated tube 770 shown in FIGS. 14 and 15 is generally cylindrical in shape, it will be appreciated that the perforated tube 770 may have a cross-section that is oval, square, rectangle, octagon, or any other suitable shape.

The perforated tube 770 includes many holes (or perforations) 772 in the tube 770. Not all of the perforations 772 are shown in FIG. 14 but it should be understood that the tube 770 may be perforated as shown in FIG. 14 at the top 778 all along the tube 770.

The perforated tube 770 defines an inside 776 of the tube 770. The tube 770 has a top and 778 and a bottom and 780. A distribution ring 782 is located at the top end 778 of the perforated tube 770. A catch basin 784 is located at the bottom end 780 of the tube 770. The catch basin 784 is configured to catch and be a reservoir for liquid 728 flowing out of the distribution ring 782 and along either the outside surface 775 or inside surface 777 of the perforated tube 770.

In some embodiments, the fluid 728 may only flow along the outer surface 775. In other embodiments, the fluid 728 may only flow along the inner surface 776. In still other embodiments, the fluid 728 flowing out of the distribution ring 782 will flow along both the outer surface 775 and inner surface 777. After the fluid 728 flows down the inner surface 777 and/or the outer surface 775, the fluid 728 will collect in the catch basin 784.

The bottom end 780 of the perforated tube 770 is located in the interior 790 a catch basin 784. In some embodiments and as shown in FIGS. 14 and 15, the catch basin 784 is annular in shape. The catch basin 784 has an outer wall 786, and inner wall 788 which defines a center portion or inner space 789. This annular shape allows fluid 728 to be collected from both the outer 775 and inner 777 walls of the perforated tube 770 while still permitting air to pass through the center portion or inner space 789 of the catch basin 790. One of ordinary skill in the art will appreciate that the geometry of the catch basin 784 may change depending upon the cross-sectional shape of the perforated tube 770.

The perforated tube 770 and catch basin 784 are located in, and supported by, the base 800. The bottom end 780 of the tube 770 and the catch basin 784 are located in the interior 802 of the base 800. The base 800 may provide a stabilizing support for the perforated tube 770 and assist in guarding against fluid 728 splashing when entering the catch basin 784.

Risers 804 may be located at the bottom of the base 800. The catch basin 784 may be supported by the risers 804. The risers 804 are arranged to allow air to flow as shown by arrows I in FIG. 15 into the interior 802 of the base 800 between the risers 804 and through the inner space 789 defined by the inner wall 788 of the catch basin 784.

A fan 806 may be located between the risers 804 in the interior 802 of the base 800. The fan 806 may be configured to direct air in the direction of into the interior 802 of the base 800 and up through the inside 776 of the tube 770 as shown by arrows I in FIG. 15. In some embodiments, a second fan 807 may be located anywhere along the length of the perforated tube 770 in order to assist airflow through the inside 776 of the tube 770. In some embodiments the second fan 807 may be located at the top of the tube 770.

The fans 806 and 807 may include a fan housing 808 and fan blades 810. A fan chord 812 may supply power to the fans 806 and 807. The fan chord 812 may also provide control signals to the fans 806 and 807 turning them on and off and/or varying their speed.

A pump and circulation system 813 may be provided to the air purifier 768 in order to circulate fluid 728 from the catch basin 784 to the distribution ring 782. The pump and circulation system 813 may include a pump 814. The pump 814 may include a filter 816 (located internally in the pump 814) configured to filter the fluid 728 flowing through the pump and circulation system 813. A pump cord 818 may be supplied to the pump 814 for supplying both power and control signals to the pump 814. A return line or conduit 820 provides fluid communication between the catch basin 784 and the fluid distribution ring 782. The return line 820 allows fluid 728 to be continuously pumped from the catch basin 784 to the distribution ring 782 where the fluid 728 flows through holes 826 in the distribution ring 782 down either the outside surface 775 or inside surface 777 of the perforated tube 770.

Ultraviolet lights 890 are located at various portions throughout the air purifier 768 in order to shine ultraviolet light onto the fluid 728. The shining ultraviolet light into the fluid 728 may serve to kill any undesirable substances in the fluid 728 such as bacteria, viruses, or any other undesirable substances in the fluid 728.

In some embodiments, the fluid 728 may be configured to flow along a metal as part of its circulation circuit to help purify the fluid 728. For example, the metal may be silver, a copper alloy, Muntz metal, a copper-zinc alloy, a copper-nickel alloy, and a copper-silicon alloy.

In operation, the pump and circulation system 813 operates the pump 814 to circulate fluid 728 out of the catch basin 784 up through the return line 720 into the distribution ring 782. Once in the distribution ring, the fluid 728 flows through holes 826 in the distribution ring 782 down the outside surface 775 and/or the inside surface 777 of the perforated tube 770. In some embodiments, the fluid 728 may only flow along the outside surface 775 or in other embodiments fluid 728 may flow only along the inside surface 777. However in other embodiments, the fluid 728 will flow along both the outside 775 and inside 777 surface of the perforated tube 770.

As the fluid 728 flows along the outside 775 and/or inside surface 777 of the perforated tube 770, the fluid 728 will flow over the holes 772 in the tube 720. At the same time air flowing through the inside 776 of the tube 720 will also flow through the holes 772 in the tube 770 as illustrated by arrows O in FIG. 15. As the air flows through the holes 772 impurities in the air may be entrapped into the fluid 728. As such, the fluid 728 acts to purify air circulating through the holes 772 in the tube 720. The fluid 728 is then purified by flowing through the filter 816 as described and being exposed to ultraviolet light provided by the LED lights 890 and or flowing over the medals described above. In this manner, the air purifier 768 may serve to purify the environment in which it is set.

In some embodiments, additives may be added to the fluid 728. The additives may help the fluid 728 stay clean, stay clear or a desired color, inhibit growth of biomatter, remain pleasant smelling or achieve any other desired attribute. For example, peroxide may be added to the fluid 728. The peroxide may react with the UV light shining on the fluid 728 maintaining the fluid 728 in a clean state.

Figure 16:
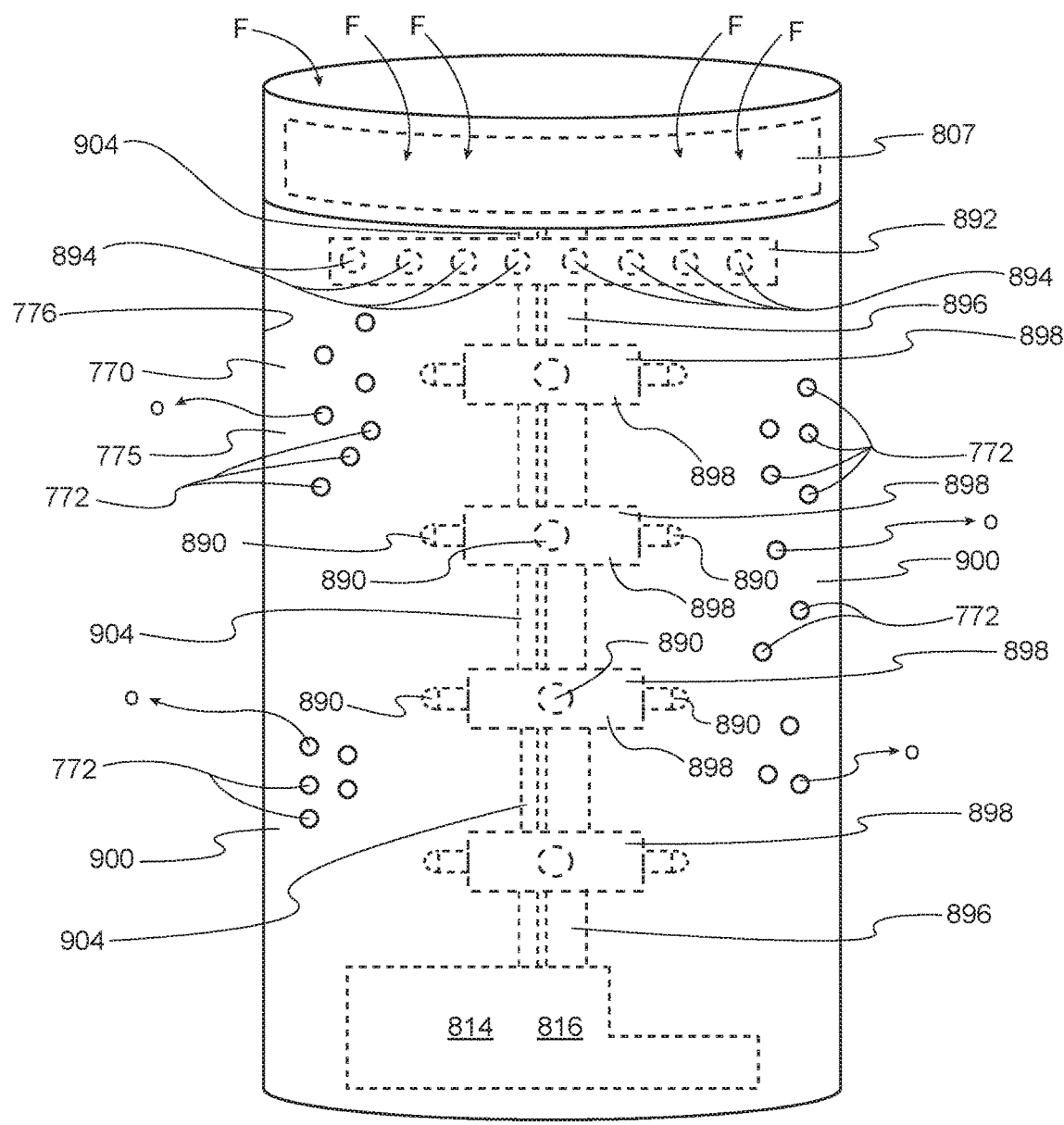
FIG. 16 is a front view of a portion of the air purifier according to an embodiment.

FIGS. 16-19 show an example embodiment where a photocatalytic material in conjunction with light is used to treat the fluid. FIG. 16 shows a perforated tube 770, although other embodiments may include a mesh screen 714, a drape 110, 425, 515 or any other structure suitable for defining a flow path for the fluid (which in many embodiments is water).

The structure 770 may include holes 772 similar to those previously described. Not all the holes 772 are illustrated in order to avoid overcrowding of the figure. In the embodiment shown in FIG. 16, a fan 807 is assembled at a top and of the perforated tube 770. The fan 870 is oriented to draw ambient air from outside of the perforated tube 770 as shown by arrows F. The air is then blown downward through the perforated tube 770 through a flow path defined by a hollow or open portion of the tube 770. Some of the air flows out of the holes 772 in the direction of arrows O. In other embodiments, the fan 807 may be oriented in opposite manner. In other words air may blow up and in the opposite direction of arrows F. In such embodiments air is drawn through the holes 772 in the opposite direction as shown by arrows O.

In either case, dust, dirt, bacteria, biomatter, viruses, insects, other impurities, or other undesired objects in the air may be deposited in the fluid flowing along the perforated tube 770 when the air (also referred herein to as a second fluid) interacts with the fluid (often water, also referred to herein as the first fluid) at, or near, the point of flowing through the holes 772. In this manner, the ambient air may be purified.

In the embodiment illustrated in FIG. 16, a distributor 904 is located inside of the perforated tube 770. The distributor 904 has holes 894 configured to spray a fluid on to the inside 776 of the perforated tube 770. As such, fluid then flows along the inside of the tube 771 a flow path defined by the inside surface 776 of the tube 770. As described in other places herein, other embodiments may use distributors 904 which allow the water or fluid to flow on the outside surface 775 as well of or instead of the inside surface 776 of the tube 770.

Similar to other embodiments described elsewhere herein, a pump mechanism 814 may pump the water from a catch basin 790 (not shown in FIG. 16.) through a filter 816 along a supply pipe or conduit 896 to the distributor 904.

The supply pipe or conduit 896 may also provide structure for mounting light bases 898. The light bases 898 may provide a support structure for supporting the lights 890. The lights 890 may be configured to shine upon the fluid as it flows along the inside surface 776 of the perforated tube 770. As mentioned elsewhere, the lights 890 may be configured to also shine upon the fluid at various other portions of the flow path of the fluid including the reservoir catch basin 790 and, in some embodiments, the outer surface 775 of the perforated tube 770.

As shown in FIG. 16, the structure 770 is coated with a photocatalytic coating 900. In some embodiments the photocatalytic coating 900 is Titanium Dioxide ($TiO_2$) on the stainless steel structure 770. Ultra Violet light, near blue, and/or visible light may be shown on the photocatalytic coating 900 to disinfect the water (first fluid) contacting the structure 770 as known in the water/fluid disinfection arts. In some embodiments, the lights 890 may emit light between and including 265 nm-550 nm. For example, at any of the following wavelengths: 265 nm, 268 nm, 365 nm, 370 nm-380 nm, 405 nm, 410 nm, 400 nm-550 nm. In some embodiments, the light source(s) may be a light emitting diode(s) (LED).

Example discussions of using light and photocatalytic coatings 900 to disinfect water may be found in an article titled "Photocatalysis of Titanium Dioxide for Water Disinfection: Challenges and Future Perspectives" by M. J. Wu, T. Bak, P. J. O'Doherty, M. C. Moffitt, J. Nowotny, T. D. Bailey and C. Kersaitis, International Journal of Photochemistry, Volume 2014 (2014), Article ID 973484, http://dx.doi.org/10.1155/2014/97348. An article titled "Titanium Dioxide Coatings on Stainless Steel (Nanotechnology)" on the what-when-how.com website http://what-when-how.com/nanoscience-and-nanotechnology/titanium-dioxide-coatings-on-stainless-steel-nanotechnology/retrieved Mar. 17, 2017; and article titled "Advanced oxidation process" on the Wikipedia website having web address: https://en.wikipedia.org/wiki/Advanced_oxidation_process. Retrieved Mar. 17, 2017. All of the articles cited in this paragraph are incorporated by reference in their entirety.

An article regarding "wet scrubbers" or Venturi Scrubbers is titled "Air Pollution Control Technology Fact Sheet" numbered EPA_452/F-03-017 and published on the Environmental Protection Agency (EPA) website: https://www3.epa.gov/ttn/catc/dir1/fventuri.pdf. Retrieved Mar. 17, 2017. This article is also incorporated by reference in its entirety.

In some embodiments, the heat generated by the lights 890 shining may move thermally to the light bases 898. The light bases 898 may be cooled by fluid flowing through the supply pipe 896. In this manner, not only does the supply pipe 896 provide conduit for the water/fluid and also to provide structure to mount the light bases 898, but also a mechanism for cooling the lights 890.

In some embodiments, an electrical cord or conduit 904 may be located near the supply pipe 896 in order to provide electricity to the lights 890 and fan 807.

Figure 17:
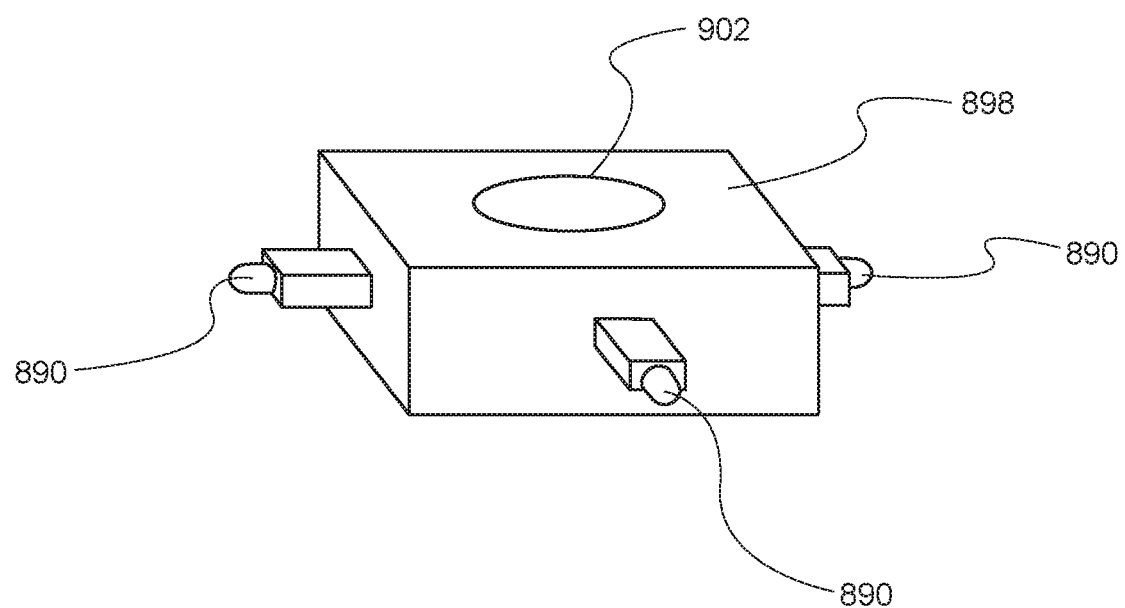
FIG. 17 is a perspective view of a light mount shown in FIG. 16.

FIG. 17 is a perspective view of a light base 898. Lights 890 which may be light emitting diodes (LEDs) are mounted to the light base 898. A center hole 902 allows the supply pipe 896 and electrical conduit 904 to pass through light base 898. The light base 898 may be mounted to the supply pipe 896 via fasteners, an adhesive(s), press fit to the supply pipe 896 or by any other suitable manner. The electrical conduit 904 is operatively connected to the lights 980 via internal or external connections for supplying power to the lights 980. The light base 898 may be made of stainless steel or other thermal conducting material to conduct heat away from the lights and to the supply pipe 896 where the heat can be transferred to the fluid in the supply pipe 896. As a result, the fluid acts as a cooling fluid for the lights 980 and the light base 898.

Figure 18:
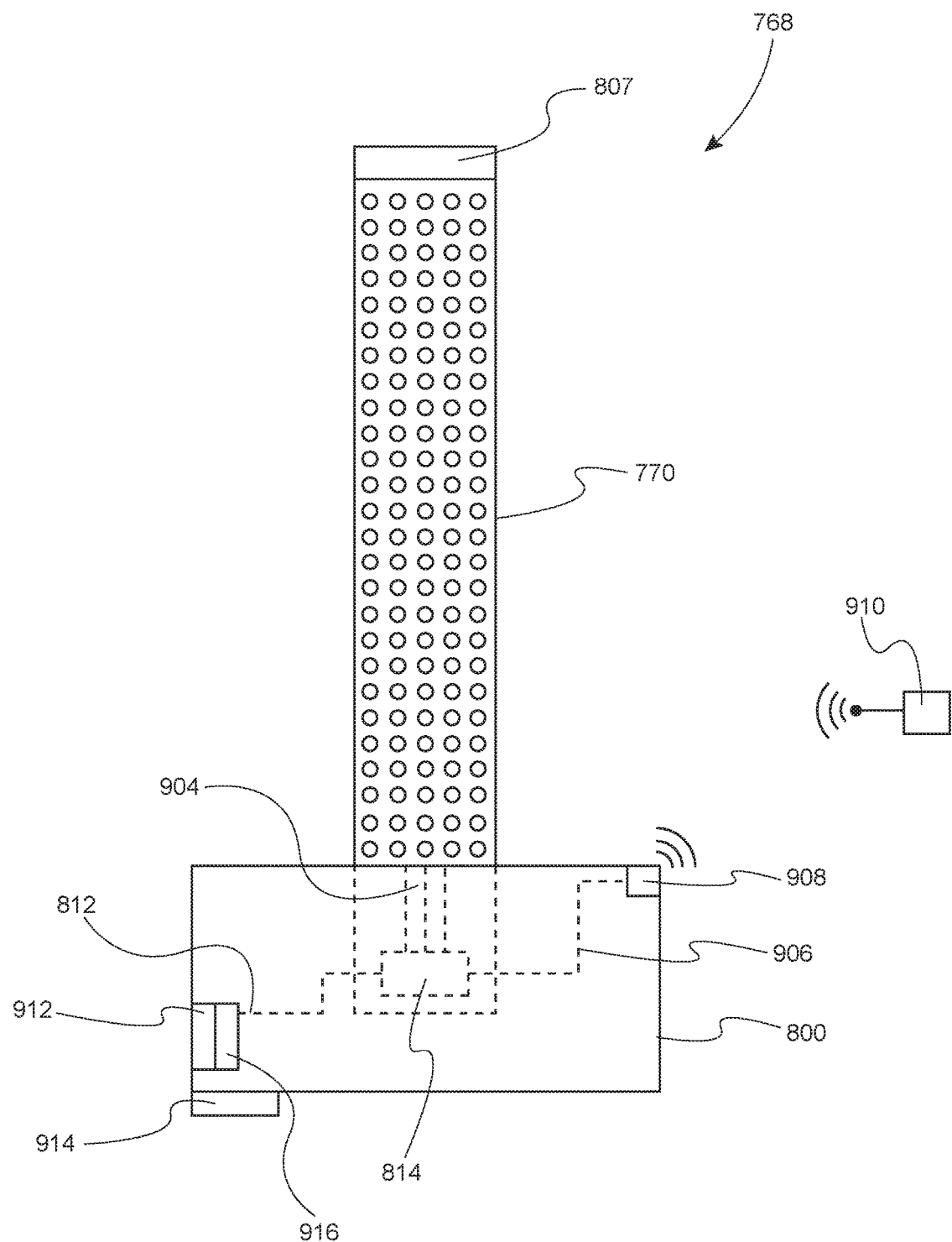
FIG. 18 is a front view of the air purifier partially shown in FIG. 16.

FIG. 18 is a side view of an air purifier 768 in accordance with the present disclosure. The air purifier 768 has a controller 908 which may be an electronic microcontroller 908. The controller 908 is operatively connected to the pump 814, lights 890 (shown in FIGS. 16 and 17), and fan 807 via the control conduit 906. The controller 908 will allow a user to the control the various aspects of the air purifier 768 in a desired manner. In other embodiments, the controller 908 may be operatively connected to the pump 814, lights 890, and fan 807 via a wireless connection.

The controller 908 may be located on the base 800 as shown or any other suitable location. The controller 908 may include various user input hardware such as buttons, a keypad, a touchscreen or any other suitable user inputs to allow a user to control the air purifier 768.

In some embodiments, a remote control 910 may wirelessly communicate with the controller 908. In such embodiments, the remote controller 910 may allow a user to operate the air purifier 768 by manipulating user inputs located on the remote controller 910. In some embodiments, the remote controller 810 may include a smart phone, a computer, a tablet computer, or any other device capable of wireless communication.

In the embodiment shown in FIG. 18, the air purifier 768 includes a battery 916 that is operatively connected via the conduit 812, and provides power to, the controller 908, the pump 814, the lights 890 (shown in FIGS. 16 and 17), and the fan 807. The battery 916 may be able to be charged conventionally via a charger cord plugged socket receiving line voltage.

In other embodiments, the battery 916 is operably connected to and charged by a power receiver 912 that receives power from a wireless charger 914. The wireless charger 914 may be a charging pad 914 over which the power receiver 912 (or battery 916) is placed. In some embodiments, the charging pad 914 uses resonant inductive coupling for inductive charging over short distances. In some embodiments, charger 914 may charge the battery 916 according to the Qi open interface standard developed by the Wireless Power Consortium for inductive charging over distances of up to 4 cm well known in the art of inductive charging. A discussion of the Qi standard may be found on the Wikipedia.com website titled "Qi (standard)" with the web address: https://en.wikipedia.org/wiki/Qi_(standard), retrieved Mar. 20, 2017 and incorporated herein by reference in its entirety. Other embodiments may use other methods of wireless charging.

Figure 19:
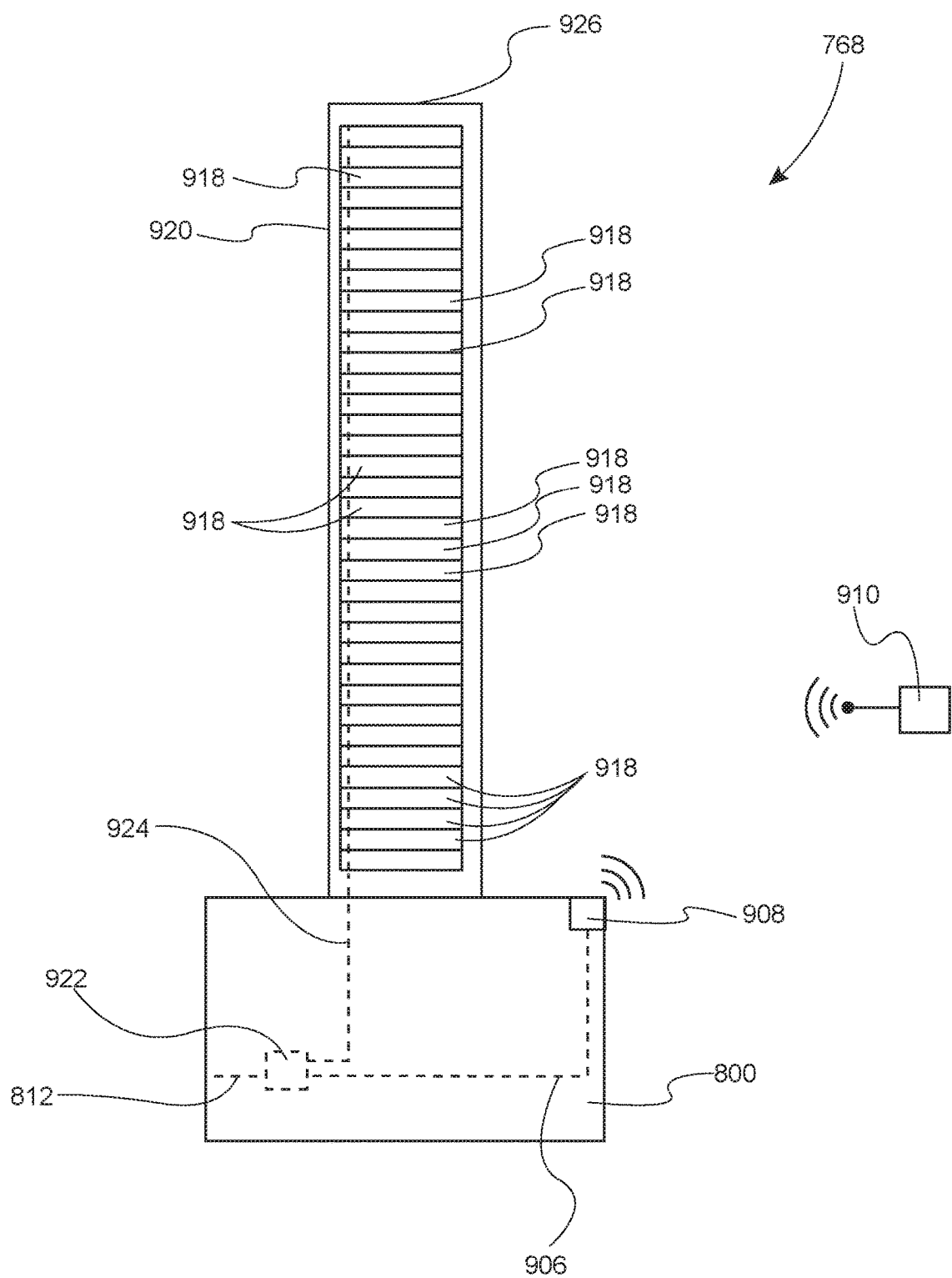
FIG. 19 is a front view of an air purifier equipped with a light shield.

FIG. 19 shows an example air purifier 768 equipped with a shield 920. The shield 920 is located on the air purifier 768 and surrounds the perforated tube or structure 770 to reduce or prevent light from the lights 890 (not shown in FIG. 19) from emitting beyond the shield 920. The shield 920 may be mounted to the base 800 or extend into the base 800. Optionally, the shield 920 may be equipped with louvers 918. The louvers 918 may allow air to pass through the shield 920 to allow the air purifier 768 to perform its desired functions while preventing or reducing light emitted by the air purifier 768 from going beyond the shield 920. In some embodiments, the air purifier 768 may have a top cap 926 which may prevent or reduce light emitted by the air purifier 768 from going beyond the shield 920.

In some embodiments, the louvers 918 may be able to be opened, closed, or moved to an intermediate position as desired. In such embodiments, the louvers 918 may be operatively connected to a louver actuating rod 924, which, in turn is controlled by a louver actuator 922. The louver actuating rod 924 may move up and down to open and close the louvers 918. The louver actuator 922 is operatively connected to the power source 916 by a conduit 812. The louver actuator 922 is operatively connected to the controller 908 by the control conduit 906. As such the louvers are opened and closed by the controller 908 or remote controller 910. The louvers 918 may be manually operated. While only the louvers 918 on the front side of the air purifier 768 are shown in FIG. 19, in some embodiments, the louvers 918 make be located on multiple sides of the air purifier 768.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A self-cleaning fountain comprising:
   a structure having two ends, defining a surface connecting the two ends for a first fluid to flow along, wherein the surface defines holes for allowing a second fluid to flow through the holes;
   a pump system configured to pump the first fluid to a first end of the structure;
   a distributer located at the first end of the structure and configured to spray the first fluid received from the pump system onto the structure;
   a catch basin located at a second end of the structure for collecting the first fluid that has moved along the surface to the catch basin;
   a photocatalytic coating on the structure; and
   a light source configured to direct light on the photocatalytic coating.

2. The self-cleaning fountain of claim 1, wherein the coating includes Titanium Dioxide.

3. The self-cleaning fountain of claim 1, wherein the structure is made of stainless steel.

4. The self-cleaning fountain of claim 1, further comprising a blower oriented to move the second fluid alone a second flow way defined, at least in part, by the structure and through the holes defined by the structure.

5. The self-cleaning fountain of claim 1, wherein the structure is any one of: a mesh and a perforated tube.

6. The self-cleaning fountain of claim 1, wherein the light source emits any one of: ultra violet, near blue light, and visible light.

7. The self-cleaning fountain of claim 1, further comprising a shield having louvers arranged on the fountain to reduce light emitting from the light source from emitting past the shield.

8. The self-cleaning fountain of claim 1, wherein the light source emits light anywhere in the range of 265 nm to 550 nm.

9. The self-cleaning fountain of claim 8, wherein the light source emits light at any of the following wavelengths: 265 nm, 268 nm, 365 nm, 370 nm-380 nm, 405 nm, 410 nm, 400 nm-550 nm.

10. The self-cleaning fountain of claim 1, wherein the light source includes a light emitting diode (LED).

11. The self-cleaning fountain of claim 1, wherein the light source is positioned to emit light on a portion of the structure where laminar flow of the first fluid occurs.

12. The self-cleaning fountain of claim 1, wherein the distributor and the structure are positioned to cause first fluid to flow along the structure due to gravity.

13. The self-cleaning fountain of claim 1, further comprising a supply conduit fluidly connected to the distributer to supply the first fluid to the distributor and the light source is connected to the supply conduit and thermally connected to the supply conduit such that when the first fluid flows through the supply conduit, the first fluid removes heat from the light source.

14. The self-cleaning fountain of claim 1, further comprising a controller configured to the control the fountain and receive input from a wireless controller.

15. The self-cleaning fountain of claim 1, further comprising:
   a battery operatively connected to at least one of the pump and the light source to provide power for at least one of the pump and the light source;
   and inductive charger operatively connected to the battery for charging the battery.

16. A method of cleaning a fluid in a fountain comprising:
   providing a first flow path for a first fluid to flow along, wherein the first flow path includes a structure defining holes;
   orienting the holes to allow a second fluid to flow through the holes and interact with the first fluid;
   providing a photocatalytic substance along the flow path to contact the first fluid; and
   orienting lights configured to activate the photocatalytic substance to provide a processing function on the first fluid.

17. The method of claim 16, further comprising: mounting the lights on a conduit for conveying the first fluid in thermal coupling such that flow of the first fluid will remove heat from the lights.

18. The method of claim 16, further comprising operatively connecting a battery to a pump system for moving the first fluid and operatively connecting the battery to an inductive charger for charging the battery.

19. A self-cleaning fountain comprising:
a structure having two ends, defining a surface connecting the two ends for a first fluid to flow along, wherein the structure defines holes for allowing a second fluid to flow through the holes;
means for moving fluid configured to move the first fluid to a first end of the structure;
a distributer located at the first end of the structure and configured to spray the first fluid received from the means for moving fluid onto the structure;
means for collecting a fluid located at a second end of the structure for collecting the first fluid that has moved along the surface to the means for collecting fluid;
a photocatalytic coating on the structure; and
means for selectively activating the photocatalytic coating to cause the photocatalytic coating to treat the first fluid.

* * * * *